(12) United States Patent
Mehra et al.

(10) Patent No.: US 11,614,447 B2
(45) Date of Patent: Mar. 28, 2023

(54) SIGNAL AMPLIFICATION IN SOLUTION-BASED PLASMONIC SPECIFIC-BINDING PARTNER ASSAYS

(71) Applicant: Zoetis Services LLC, Parsippany, NJ (US)

(72) Inventors: Rajesh K. Mehra, Parsippany, NJ (US); Vincent Chiang, Parsippany, NJ (US); Kenneth Aron, Parsippany, NJ (US); Jessica Frisz, Parsippany, NJ (US)

(73) Assignee: Zoetis Services LLC, Parsippany, NJ (US)

( * ) Notice: Subject to any disclaimer, the term of this patent is extended or adjusted under 35 U.S.C. 154(b) by 0 days.

(21) Appl. No.: 17/536,520

(22) Filed: Nov. 29, 2021

(65) Prior Publication Data

US 2022/0082562 A1    Mar. 17, 2022

Related U.S. Application Data

(63) Continuation of application No. 16/545,019, filed on Aug. 20, 2019, now Pat. No. 11,215,614, which is a
(Continued)

(51) Int. Cl.
*G01N 33/553* (2006.01)
*G01N 33/543* (2006.01)

(52) U.S. Cl.
CPC ..... *G01N 33/553* (2013.01); *G01N 33/54373* (2013.01); *G01N 2469/10* (2013.01); *Y02A 50/30* (2018.01)

(58) Field of Classification Search
None
See application file for complete search history.

(56) References Cited

U.S. PATENT DOCUMENTS 4,704,366 A    11/1987   Juarez-Salinas et al.
5,061,381 A    10/1991   Burd
(Continued)

FOREIGN PATENT DOCUMENTS

CN    1417586 A    5/2003
CN    1798976 A    7/2006
(Continued)

OTHER PUBLICATIONS

Atanasov, P.A. et al., "Noble metallic nanostructures: preparation, properties, applications", Journal of Physics: Conference Series 514 (2014), pp. 1-8.
(Continued)

*Primary Examiner* — Rebecca M Giere
(74) *Attorney, Agent, or Firm* — Cooley LLP

(57) ABSTRACT

The present invention relates to analyte detection devices and methods of using such devices to detect minute quantities of a target analyte in a sample. In particular, the invention provides a method of detecting a target analyte in a sample comprising mixing the sample with a first detection conjugate and a second detection conjugate in solution, wherein the first and second detection conjugates comprise metallic nanostructures coupled to binding partners that are capable of specifically binding to the target analyte if present in the sample to form a complex between the first detection conjugate, the analyte, and the second detection conjugate, wherein a change in an optical signal upon complex formation indicates the presence of the target analyte in the sample. Methods of preparing nanostructures and nanoalloys, as well as nanostructures and nanoalloys conjugated to binding partners, are also described.

24 Claims, 22 Drawing Sheets

Related U.S. Application Data continuation of application No. 15/799,320, filed on Oct. 31, 2017, now Pat. No. 10,429,383, which is a continuation of application No. 15/228,491, filed on Aug. 4, 2016, now Pat. No. 9,835,622.

(60) Provisional application No. 62/201,051, filed on Aug. 4, 2015.

(56) References Cited

U.S. PATENT DOCUMENTS

| | | | |
|---|---|---|---|
| 5,122,284 A | 6/1992 | Braynin et al. |
| 5,186,844 A | 2/1993 | Burd et al. |
| 5,304,348 A | 4/1994 | Burd et al. |
| 5,457,053 A | 10/1995 | Burd et al. |
| 5,624,597 A | 4/1997 | Buhl et al. |
| 5,693,233 A | 12/1997 | Schembri |
| 5,939,021 A | 8/1999 | Hansen et al. |
| 6,579,726 B1 | 6/2003 | Natan et al. |
| 6,660,381 B2 | 12/2003 | Halas et al. |
| 6,685,986 B2 | 2/2004 | Oldenburg et al. |
| 6,699,724 B1 | 3/2004 | West et al. |
| 6,861,263 B2 | 3/2005 | Natan |
| 6,970,239 B2 | 11/2005 | Chan et al. |
| 7,135,054 B2 | 11/2006 | Jin et al. |
| 7,144,627 B2 | 12/2006 | Halas et al. |
| 7,212,692 B2 | 5/2007 | Yan |
| 7,307,731 B2 | 12/2007 | Naya |
| 7,405,054 B1 | 7/2008 | Hasenbank et al. |
| 7,648,595 B2 | 1/2010 | Jin et al. |
| 7,732,145 B2 | 6/2010 | Kang et al. |
| 7,790,066 B2 | 9/2010 | Wang et al. |
| 7,807,633 B2 | 10/2010 | Haynie |
| 8,101,424 B2 | 1/2012 | Geddes |
| 8,110,250 B2 | 2/2012 | Ojima et al. |
| 8,263,418 B2 | 9/2012 | Brennan et al. |
| 8,426,152 B2 | 4/2013 | Gerion et al. |
| 8,597,897 B2 | 12/2013 | Kim et al. |
| 8,628,727 B2 | 1/2014 | Van Duyne et al. |
| 8,697,129 B2 | 4/2014 | Qian et al. |
| 8,753,559 B2 | 6/2014 | Yang et al. |
| 8,784,895 B2 | 7/2014 | Messersmith et al. |
| 8,808,420 B2 | 8/2014 | Aherne et al. |
| 9,034,656 B2 | 5/2015 | Mehra et al. |
| 9,040,310 B2 | 5/2015 | Ashworth-Sharpe et al. |
| 9,217,746 B2 | 12/2015 | Geddes |
| 9,308,582 B2 | 4/2016 | Sun et al. |
| 9,835,622 B2 | 12/2017 | Mehra et al. |
| 9,921,218 B2 | 3/2018 | Mehra et al. |
| 10,281,465 B2 | 5/2019 | Mehra et al. |
| 10,429,383 B2 | 10/2019 | Mehra et al. |
| 10,488,409 B2 | 11/2019 | Mehra et al. |
| 11,209,430 B2 | 12/2021 | Mehra et al. |
| 11,215,614 B2 | 1/2022 | Mehra et al. |
| 11,255,854 B2 | 2/2022 | Mehra et al. |
| 2001/0002315 A1 | 5/2001 | Schultz et al. |
| 2005/0037437 A1* | 2/2005 | Zeidler ............ G01N 33/5076 435/7.2 |
| 2006/0240573 A1 | 10/2006 | Kao et al. |
| 2006/0246513 A1 | 11/2006 | Bohannon |
| 2007/0054337 A1 | 3/2007 | Ferning et al. |
| 2007/0092978 A1 | 4/2007 | Mink et al. |
| 2008/0213814 A1 | 9/2008 | Gerion et al. |
| 2008/0227219 A1 | 9/2008 | Gamez |
| 2009/0018025 A1 | 1/2009 | Shao et al. |
| 2010/0028410 A1 | 2/2010 | Haynie |
| 2010/0062545 A1 | 3/2010 | Geddes |
| 2010/0120057 A1 | 5/2010 | Mehra et al. |
| 2010/0136566 A1 | 6/2010 | Mehra et al. |
| 2010/0159441 A1 | 6/2010 | Chiang et al. |
| 2010/0184086 A1 | 7/2010 | Callister |
| 2011/0065088 A1 | 3/2011 | Kang et al. |
| 2011/0124125 A1 | 5/2011 | Mehra et al. |
| 2011/0136143 A1 | 6/2011 | Castro et al. |
| 2011/0136155 A1 | 6/2011 | Mehra et al. |
| 2011/0275061 A1 | 11/2011 | Weidemaier et al. |
| 2012/0101007 A1 | 4/2012 | Ahern et al. |
| 2012/0162640 A1 | 6/2012 | Sakagami |
| 2012/0208174 A1 | 8/2012 | Galush et al. |
| 2012/0219966 A1 | 8/2012 | Kawamura |
| 2012/0252005 A1 | 10/2012 | Chiang et al. |
| 2013/0034854 A1 | 2/2013 | Ashworth-Sharpe et al. |
| 2013/0115634 A1 | 5/2013 | Mehra et al. |
| 2013/0130404 A1 | 5/2013 | Mehra et al. |
| 2013/0172207 A1 | 7/2013 | Dai et al. |
| 2013/0189793 A1 | 7/2013 | Qian et al. |
| 2013/0203075 A1 | 8/2013 | Svenson et al. |
| 2013/0230717 A1 | 9/2013 | Xia et al. |
| 2013/0252275 A1 | 9/2013 | Tokonami et al. |
| 2014/0105982 A1 | 4/2014 | Oldenburg et al. |
| 2014/0121125 A1 | 5/2014 | Mehra et al. |
| 2014/0162067 A1 | 6/2014 | Shahjamali et al. |
| 2014/0170070 A1 | 6/2014 | Qian et al. |
| 2014/0272932 A1 | 9/2014 | Muerhoff et al. |
| 2014/0272933 A1 | 9/2014 | Dawson et al. |
| 2014/0308756 A1 | 10/2014 | Gautier et al. |
| 2014/0349317 A1 | 11/2014 | Kobayashi |
| 2015/0004102 A1 | 1/2015 | Salman et al. |
| 2015/0017258 A1 | 1/2015 | El-Said et al. |
| 2015/0038355 A1 | 2/2015 | Tan et al. |
| 2015/0212005 A1 | 7/2015 | Akhavan-Tafti et al. |
| 2015/0247846 A1 | 9/2015 | Gerion et al. |
| 2015/0293088 A1 | 10/2015 | Mehra et al. |
| 2016/0047804 A1 | 2/2016 | Mehra et al. |
| 2016/0120978 A1 | 5/2016 | Guler et al. |
| 2016/0153972 A1 | 6/2016 | Daynes et al. |
| 2016/0202251 A1 | 7/2016 | Goh et al. |
| 2017/0038366 A1 | 2/2017 | Mehra et al. |
| 2018/0059104 A1 | 3/2018 | Mehra et al. |
| 2018/0156790 A1 | 6/2018 | Mehra et al. |
| 2019/0219572 A1 | 7/2019 | Mehra et al. |
| 2020/0110086 A1 | 4/2020 | Mehra et al. |
| 2022/0074934 A1 | 3/2022 | Mehra et al. |
| 2022/0091113 A1 | 3/2022 | Mehra et al. |

FOREIGN PATENT DOCUMENTS

| | | |
|---|---|---|
| CN | 101296945 A | 10/2008 |
| CN | 102103145 A | 6/2011 |
| CN | 103335984 A | 10/2013 |
| CN | 104105965 B | 7/2016 |
| JP | H07501880 A | 2/1995 |
| JP | H10132818 A | 5/1998 |
| JP | 2000028612 A | 1/2000 |
| JP | 2000028614 A | 1/2000 |
| JP | 2000146959 A | 5/2000 |
| JP | 2001513198 A | 8/2001 |
| JP | 2003514224 A | 4/2003 |
| JP | 2005195440 A | 7/2005 |
| JP | 2005520125 A | 7/2005 |
| JP | 2007114129 A | 5/2007 |
| JP | 2008527332 A | 7/2008 |
| JP | 2009516199 A | 4/2009 |
| JP | 2009150708 A | 7/2009 |
| JP | 2010286331 A | 12/2010 |
| JP | 2010537155 A | 12/2010 |
| JP | 2011525966 A | 9/2011 |
| JP | 2012132875 A | 7/2012 |
| JP | 2012215472 A | 11/2012 |
| JP | 2013525800 A | 6/2013 |
| JP | 2014228385 A | 12/2014 |
| JP | 20157652 A | 1/2015 |
| JP | 2015507078 A | 3/2015 |
| JP | 2015509936 A | 4/2015 |
| JP | 2016510126 A | 4/2016 |
| TW | 201408690 A | 3/2014 |
| WO | WO-0109388 A1 | 2/2001 |
| WO | WO-03008539 A2 | 1/2003 |
| WO | WO-2006074076 A1 | 7/2006 |
| WO | WO-2007047924 A2 | 4/2007 |
| WO | WO-2007053201 A2 | 5/2007 |
| WO | WO-2007061793 A2 | 5/2007 |
| WO | WO-2008086054 A2 | 7/2008 |
| WO | WO-2008116093 A2 | 9/2008 |

(56) References Cited

FOREIGN PATENT DOCUMENTS

| | | |
|---|---|---|
| WO | WO-2009117510 A2 | 12/2009 |
| WO | WO-2010006201 A2 | 1/2010 |
| WO | WO-2011095636 A1 | 8/2011 |
| WO | WO-2011063003 A2 | 9/2011 |
| WO | WO-2011063235 A2 | 10/2011 |
| WO | WO-2011139792 A2 | 11/2011 |
| WO | WO-2011148870 A1 | 12/2011 |
| WO | WO-2012077756 A1 | 6/2012 |
| WO | WO-2013067524 A1 | 5/2013 |
| WO | WO-2013078227 A1 | 5/2013 |
| WO | WO-2013169640 A1 | 11/2013 |
| WO | WO-2014020293 A1 | 2/2014 |
| WO | WO-2014059274 A1 | 4/2014 |
| WO | WO-2015160923 A1 | 10/2015 |
| WO | WO-2016007942 A1 | 1/2016 |
| WO | WO-2016134214 A1 | 8/2016 |
| WO | WO-2016025703 A2 | 9/2016 |
| WO | WO-2016170183 A1 | 10/2016 |
| WO | WO-2017024163 A1 | 2/2017 |
| WO | WO-2018140953 A1 | 8/2018 |

OTHER PUBLICATIONS

[Author Unknown], Alpha Protein-Protein Interaction User Guide, PerkinElmer Japan, Nov. 2017, 40 pages, https://www.perkinelmer.co.jp/Portals/0/resource/tech/tech_Is/protocol_collection/Alph_a_Protein-Protein_Interaction_userguide.pdf.

[Author Unknown], "Sorvall Legend XT Sorvall Legend XTR Instruction Manual," Thermo Fisher Scientific, No. 50119927-4, Feb. 14, 2011 (Feb. 14, 2011), pp. 1-59. Retrieved from the Internet: http://core.phmtox.msu.edu/Scheduling/ItemDocs/40/XTR_Manual.pdf on Mar. 7, 2018 (Mar. 7, 2018).

Bangs Laboratories, Inc., "Lateral Flow Tests," TechNote 303, available at http://www.bangslabs.com/sites/default/files/bangs/docs/pdf/303.pdf, 1999. 6 pages.

Bolduc and Masson, "Advances in surface plasmon resonance sensing with nanoparticles and thin films: nanomaterials, surface chemistry, and hybrid plasmonic techniques." Anal Chem. (2011); 83 (21): 8057-8062. Epub Aug. 29, 2011.

Bui, et al., "Gold Nanoparticle Aggregation-Based Highly Sensitive DNA Detection Using Atomic Force Microscopy," Anal. Bioanal. Chem., vol. 388: 1185-1190, 2007.

Cui, et al., "Synthesis of AgcoreAushell Bimetallic Nanoparticles for Immunoassay Based on Surface-Enhanced Raman Spectroscopy". J Phys Chem B. (Mar. 9, 2006); 110(9): 4002-4006.

Dong, P., et al., "Ultrathin Gold-Shell Coated Silver Nanoparticles onto a Glass Platform for Improvement of Plasmonic Sensors." ACS Appl. Mater. Interfaces (2013); 5 (7): 2392-2399.

European Patent Application No. 12852350.3, Extended European Search Report dated May 13, 2015, 10 pages.

European Patent Application No. 15831667.9, Supplementary European Search Report dated Nov. 30, 2017, 9 pages.

European Patent Application No. 16833889.5, Extended European Search Report dated Dec. 21, 2018, 7 pages.

European Patent Application No. 18196372.9, Extended European Search Report dated Feb. 21, 2019, 13 pages.

European Patent Application No. 18745189.3, Extended Supplementary European Search Report dated Dec. 2, 2020, 16 pages.

European Patent Application No. 18745189.3, Partial Supplementary European Search Report dated Aug. 27, 2020, 20 pages.

European Patent Application No. 21177342.9, Extended European Search Report dated Dec. 23, 2021, 15 pages.

Fan, Chao-Ming et al. "A study of double antigen sandwich colloidal gold immunochromatography rapid detection for *Mycobacterium tuberculosis* antibody", US National Library of Medicine Database accession No. NLM21729624 (May 2011), 2 pages.

Gupta, R. et al., "Preparation and characterization of surface plasmon resonance tunable gold and silver films", Journal of Applied Physics (2002), 92(9): 5264-5271.

Gupta, S. et al., "Characterization and optimization of gold nanoparticle-based silver-enhanced immunoassays", Anal. Chem. (2007), 79: 3810-3820.

Haes, A., et al., "Nanoscale plasmonics begins to unravel Alzheimer's disease", LaserFocusWorld, Jun. 1, 2005, www.laserfocusworld.com/test-measurement/research/article/16555980/nanoscale-plasmonics-begins-to-unravel-alzheimers-disease#:~:text=Nanoscale%20plasmonics%20begins%20to%20unravel%20Alzheimer%E2%80%99s%20disease%20An,an%20Alzheimer%E2%80%99s%20clinical%20diagnostic%20test.%20Jun%201st%2C%202005, 10 pages.

Helmerhorst, E. et al., "Real-time and label-free bio-sensing of molecular interactions by surface plasmon resonance: A Laboratory Medicine Perspective", Clin Biochem Rev (2012), 33: 161-173.

Hong, W. et al. "Development of an up-converting phosphor technology-based 10-channel lateral flow assay for profiling antibodies against Yersinia pestis", J Microbiol Methods (2010), 83(2): 133-140.

Howes, et al., "Bionanotechnology. Colloidal nanoparticles as advanced biological sensors". Science (Oct. 3, 2014); 346(6205): 1247390. Epub Oct. 2, 2014.

Jana D., et al., "Capping Agent-Free Gold Nanostars Show Greatly Increased Versatility and Sensitivity for Biosensing," Analytical Chemistry, 2015, vol. 87(7), pp. 3964-3972.

Jana, et al., Supporting Information for "Capping Agent-Free Gold Nanostars Show Greatly Increased Versatility and Sensitivity for Biosensing". Anal. Chem. (2015); 87 (7): 3964-3972, 11 pages.

Jia, K., et al., "Strong Improvements of Localized Surface Plasmon Resonance Sensitivity by Using Au/Ag Bimetallic Nanostructures Modified with Polydopamine Films." ACS Appl. Mater. Interfaces (2014); 6 (1): 219-227.

Kvtek, O., et al., "Noble metal nanostructures influence of structure and environment on their optical properties." Journal of Nanomaterials (2013); vol. 2013, Article ID 743684, pp. 1-15, 16 pages.

LamdaGen. Plasmonic ELSA. [online] Apr. 21, 2014 [retrieved Nov. 27, 2015]. Available on the internet at URL:http://web.archive.org/web/20140421112507/http://lamdagen.eom/lspr-verview/plasmonic-elisa/, 1 page.

Li, M. et al., "Three-dimensional hierarchical plasmonic nano-architecture enhanced surface-enhanced raman scattering immunosensor for cancer biomarker detection in blood plasma", ACS Nano. (2013), 7(6): 4967-4976.

Lyon, et al., "Colloidal Au-Enhanced Surface Plasmon Resonance Immunosensing". Anal. Chem. (1998); 70: 5177-5183.

Mohammed and Desmulliez, "Lab-on-a-chip based immunosensor principles and technologies for the detection of cardiac biomarkers: A Review", Lab Chip (2011), 11 (4): 569-595.

Moreton, et al., "Functionalization of Hollow Gold Nanospheres for use as Stable, Red-shifted SERS Nanotags". The Royal Society of Chemistry (2013); 7(14): 6075-6082, 8 pages, published on Mar. 6, 2015.

Mott, et al., "A Study on the Plasmonic Properties of Silver Core Gold Shell Nanoparticles: Optical Assessment of the Particle Structure". Japanese Journal of Applied Physics (Jun. 20, 2011); vol. 50, No. 6R, 8 pages.

Mott, et al., "Synthesis of Size and Shape Controlled Silver Nanoparticles Coated by a Thin Layer of Gold and Their Use as Ultrasensitive Biomolecular Probes." Mater. Res. Soc. Symp. Proc. (2010); Materials Research Society 1253-K09-04, vol. 1253, 6 pages.

Murshid, et al., "Gold plating of silver nanoparticles for superior stability and preserved plasmonic and sensing properties". Chem Commun. (Dec. 18, 2013); 49(97): 11355-11357.

Nitin, et al., "Oligonucleotide-Coated Metallic Nanoparticles as a Flexible Platform for Molecular Imaging Agents," Bioconjug. Chem. (2007); vol. 18(6): 2090-2096.

Oh, Bo-Ram et al., "Integrated nanoplasmonic sensing for cellular functional immunoanalysis using human blood", ACS Nano. (2014), 8(3): 2667-2676.

Park, et al., "Nanostar Clustering Improves the Sensitivity of Plasmonic Assays". Bioconjug Chem. (Aug. 19, 2015); 26(8): 1470-1474. Epub Jul. 2, 2015.

Paul, S. et al., "Surface plasmon resonance imaging detection of silver nanoparticle-tagged immunoglobulin", J. R. Soc. Interface (2011), 8: 1204-1211.

(56) References Cited

OTHER PUBLICATIONS

PCT/US2012/066108, International Preliminary Report on Patentability, dated May 27, 2014, 7 pages.
PCT/US2012/066108, International Search Report and Written Opinion, dated Mar. 25, 2013, 10 pages.
PCT/US2012/066108, Invitation to Pay Additional Fees, dated Jan. 8, 2013, 2 pages.
PCT/US2015/045041, International Preliminary Report on Patentability, dated Feb. 14, 2017, 8 pages.
PCT/US2015/045041, International Search Report and Written Opinion, dated Jul. 26, 2016, 13 pages.
PCT/US2015/045041, Invitation to Pay Additional Fees, dated Oct. 20, 2015, 3 pages.
PCT/US2016/045606, International Preliminary Report on Patentability, dated Feb. 6, 2018, 9 pages.
PCT/US2016/045606, International Search Report, dated Oct. 24, 2016, 2 pages.
PCT/US2016/045606, Written Opinion, dated Oct. 24, 2016, 8 pages.
PCT/US2018/015981, International Preliminary Report on Patentability, dated Jul. 30, 2019, 15 pages.
PCT/US2018/015981, International Search Report and Written Opinion, dated Apr. 13, 2018, 22 pages.
Pei et al., "Highly sensitive SERS-based immunoassay with simultaneous utilization of self-assembled substrates of gold nanostars and aggregates of gold nanostar". Journal of Materials Chemistry B (2013); 1(32): 3992-3998.
Raphael, M.P. et al., "Quantitative LSPR imaging for biosensing with single nanostructure resolution", Biophysical Journal (2013), 104(1): 30-36.
Riskin, et al., "Ultrasensitive Surface Plasmon Resonance Detection of Trinitrotoluene by a Bis-aniline-Cross-Linked Au Nanoparticles Composite". JACS (2009); 131:7368-7378.
Ruemmele, J.A. et al., "A localized surface plasmon resonance imaging instrument for multiplexed biosensing", Anal Chem. (2013), 85(9): 4560-4566.
Seekell, K. et al., "Optimization of immunolabeled plasmonic nanoparticles for cell surface receptor analysis", Methods. (2012), 56(2): 310-316.
Shao, Y. et al., "Optical fiber LSPR biosensor prepared by gold nanoparticle assembly on polyelectrolyte multilayer", Sensors (2010), 10: 3585-3596.

Singh, et al., "Intensification of surface enhanced Raman scattering of thiol-containing molecules using Ag@Au core@shell nanoparticles". Journal of Applied Physics (2011); 109 (9): 1-38, 094301. Epub May 2, 2011.
Song, et al., "Gold-modified silver nanorod arrays for SERS-based immunoassays with improved sensitivity", Journals of Materials Chemistry B (Nov. 1, 2014); 2(43): 7488-7494.
Sotiriou, et al., "Plasmonic biocompatible silver-gold alloyed nanoparticles", Chem Commun (Camb). (Nov. 14, 2014); 50(88): 13559-13562.
Stringer et al., "Development of an optical biosensor using gold nanoparticles and quantum dots for the detection of Porcine Reproductive and Respiratory Syndrome Virus", Sensors and Actuators B: Chemical (2008), 134(2): 427-431.
Tauran, Y. et al., "Molecular recognition by gold, silver and copper nanoparticles", World J Biol Chem. (2013), 4(3): 35-63.
Tokel, O. et al., "Advances in plasmonic technologies for point of care applications", Chem Rev. (2014), 114(11): 5728-5752.
Truong, P.L., et al., "A new method for non-labeling attomolar detection of diseases based on an individual gold nanorod immunosensor." Lab Chip (2011); 11: 2591-2597.
Walters and Parkin, "The incorporation of noble metal nanoparticles into host matrix thin films: synthesis, characterisation and applications", J. Mater. Chem. (2009), 19: 574-590.
Wu, et al., "Bioassay of prostate-specific antigen (PSA) using microcantilevers." Nature Biotechnology (2001); 19: 856-860.
Wu et al., "Gold Nanoparticle-Based Enzyme-Linked Antibody-Aptamer Sandwich Assay for Detection of *Salmonella typhimurium*." ACS Applied Materials and Interfaces (2014); 6: 16974-16981.
Zhang and Cremer, "Interactions between macromolecules and ions: the Hofmeister series." Blood (2006); 10 (6): 658-663.
Zheng, et al., "[Gold Nanoparticles-Based Localized Surface Plasmon Resonance Scattering Analysis Method for the Determination of Trace Amounts of Hg(II)]". Spectroscopy and Spectral Analysis (Jun. 2014); 34(6): 1477-1481.
[Author Unknown], Alpha Assays Protein: Protein Interaction User Guide, PerkinElmer, Waltham, MA, USA, May 2011, 40 pages, https://www.blossombio.com/pdf/products/UG_Alphatech.pdf.
Shkilnyy, A. et al., "Poly(ethylene glycol)-stabilized silver nanoparticles for bioanalytical applications of SERS spectroscopy", Analyst (Jan. 1, 2009); vol. 134, No. 9, p. 1868-1872. Epub Jul. 6, 2009.

\* cited by examiner

FIG. 6
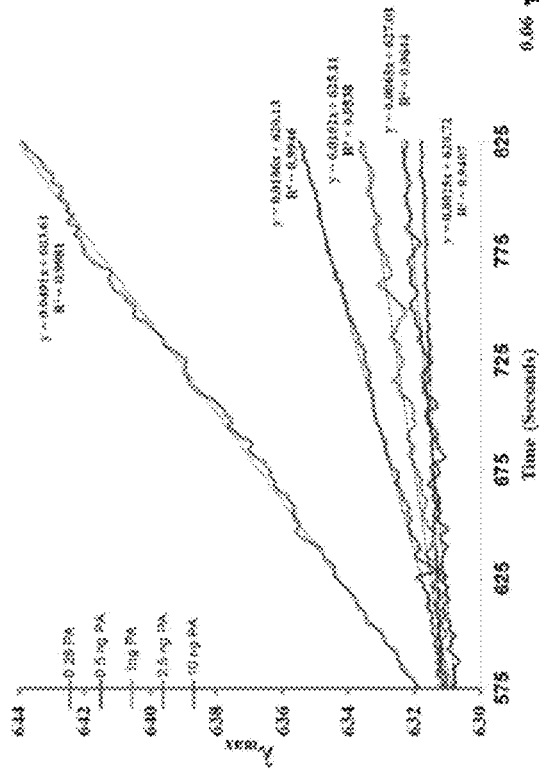
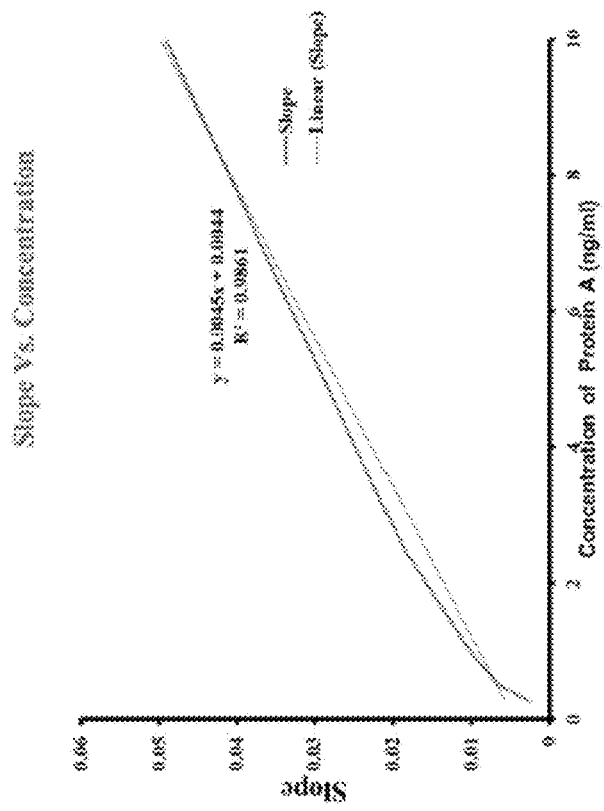

FIG. 9C

| | 0 ng/ml | 0.5 ng/ml | 2.5 ng/ml | 5 ng/ml |
|---|---|---|---|---|
| 30%C1+70%C6 PBS-BSA | 62.8 | 104.1 | 222.3 | 394.6 |
| 30%C1+70%C6 PEG buffer | -194.4 | -80.6 | 369.7 | 920.4 |
| 50%C1+50%C6 PBS-BSA | 91.2 | 119.4 | 270.0 | 470.2 |

…

SIGNAL AMPLIFICATION IN SOLUTION-BASED PLASMONIC SPECIFIC-BINDING PARTNER ASSAYS

CROSS REFERENCE TO RELATED APPLICATIONS

The present application is a continuation of U.S. patent application Ser. No. 16/545,019, filed Aug. 20, 2019, which is a continuation of U.S. patent application Ser. No. 15/799,320, filed Oct. 31, 2017 (now U.S. Pat. No. 10,429,383, issued Oct. 1, 2019), which is a continuation of U.S. patent application Ser. No. 15/228,491, filed on Aug. 4, 2016 (now U.S. Pat. No. 9,835,622, issued Dec. 5, 2017) and claims the benefit of priority of U.S. Provisional Application No. 62/201,051, filed on Aug. 4, 2015, the contents of which are hereby incorporated by reference in their entireties.

FIELD OF THE INVENTION

The present invention relates to systems and methods for detecting target analytes in a sample. In particular, the present invention provides a localized plasmon resonance-based analyte detection system capable of detecting a minute quantity of a target analyte in a sample.

BACKGROUND OF THE INVENTION

Current immunoassays and biomolecule binding assays typically require multiple steps and sophisticated equipment to perform the assays. The lack of sensitivity and the complexity involved in performing such heterogeneous assays arises from the specific need to separate labeled from unlabeled specific binding partners.

Attempts to develop assays based on the local surface plasmon resonance (LSPR) properties of noble metal nanoparticles have been made (Tokel et al., Chem Rev., Vol. 114: 5728-5752, 2014). LSPR is the collective oscillation of electrons in nanometer-sized structures induced by incident light. Metallic nanoparticles have a strong electromagnetic response to refractive index changes in their immediate vicinity and thus shifts in the resonance frequency of the nanoparticles can be measured as an indicator of molecules binding to the nanoparticle surface. Although metallic nanoparticles, particularly gold nanoparticles, have been employed in diagnostic assays to detect binding events, such assays generally suffer from low sensitivity and cannot be used to quantitatively monitor the kinetics of sequential binding events.

Thus, improved assay methods employing a homogenous format while providing increased sensitivity are needed. Assays utilizing standard laboratory techniques, such as spectroscopy, would also be desirable.

SUMMARY OF THE INVENTION

The present application describes the use of localized surface plasmon resonance (LSPR) techniques for performing assays involving specific binding partners including, but not limited to, ligands, receptors, transcription factors, binding DNA elements, antigens, and antibodies. More specifically, the present application relates to processes and materials for achieving significant amplification in such assays using composite metallic nanomaterial labeled partners.

In various embodiments described herein, the present application relates to the use of composite nanomaterial labeled partners in solution to determine the binding of specific binding partners in a qualitative or quantitative manner.

In a first aspect, the present application provides methods of detecting a target analyte in a sample. In one embodiment, the methods comprise mixing the sample with a first detection conjugate and a second detection conjugate, wherein the first and second detection conjugates comprise metallic nanostructures coupled to binding partners that are capable of specifically binding to the target analyte if present in the sample to form a complex between the first detection conjugate, the analyte, and the second detection conjugate; exposing the complex to a light source at a wavelength range within the ultraviolet-visible-infrared spectrum; and measuring an optical signal from the complex, wherein a change in the optical signal indicates the presence of the target analyte in the sample. In an exemplary embodiment, the metallic nanostructure in the first detection conjugate and/or the second detection conjugate is a composite metallic nanostructure. In another exemplary embodiment, the step of mixing occurs in the presence of a polymeric material selected from polyethylene glycol (PEG), polyvinylpyrrolidone, polyallylamine, polyethyleneimine, polylysine, polyacrylic acid, polyvinylalcohol, and polyaspartic acid. In a preferred embodiment, the polymeric material is PEG. In yet another exemplary embodiment, the step of mixing occurs in the presence of a polysaccharide. In some embodiment, the polysaccharide is selected from maltodextrin, corn syrup, and polyglucose. In a preferred embodiment, the polysaccharide is maltodextrin. In yet another exemplary embodiment, the step of mixing occurs in the presence of a blocking agent. In some embodiments, the blocking agent is selected from bovine serum albumin, casein, gelatin, ovalbumin, and gamma-globulins. In a preferred embodiment, the blocking agent is bovine serum albumin.

In some embodiments, the detection conjugates comprise binding partners that are capable of specifically binding to a target analyte. In certain embodiments, the binding partners are haptens and other small molecules, drugs, hormones, biological macromolecules including, but not limited to, antibodies or fragments thereof (e.g., Fv, Fab, (Fab)$_2$, single chain, CDR etc.), antigens, receptors, ligands, polynucleotides, aptamers, polypeptides, polysaccharides, lipopolysaccharides, glycopeptides, lipoproteins, or nucleoproteins. In certain exemplary embodiments, the binding partners are antibodies. In other exemplary embodiments, the binding partners are antigens. In some embodiments, the detection conjugates (e.g., a first detection conjugate and a second detection conjugate) comprise binding partners that are the same type of molecule.

In some embodiments, the metallic nanostructures in the detection conjugates can be composed of a noble metal or composite thereof. In some embodiments, the metallic nanostructures in the detection conjugates may be composed of a transition metal or composite thereof. In some embodiments, the metallic nanostructures in the detection conjugates may comprise an alkali metal or lanthanide in combination with a noble or transition metal. In certain embodiments, metallic nanostructures in the detection conjugates comprise a metal selected from gold, silver, copper, platinum, palladium, ruthenium, rhodium, osmium, iridium, titanium, chromium, cadmium, zinc, iron, cobalt, nickel, and composites thereof. In an exemplary embodiment, the metallic nanostructures are gold nanostructures. In another exemplary embodiment, the metallic nanostructures are silver nanostructures.

In preferred embodiments, the metallic nanostructures in the detection conjugates are composite metallic nanostructures that comprise at least two noble metals, transition metals, alkali metals, or lanthanides. In some embodiments, the composite metallic nanostructures comprise at least two metals selected from gold, silver, copper, platinum, palladium, ruthenium, rhodium, osmium, iridium, titanium, chromium, cadmium, zinc, iron, cobalt, and nickel. In other embodiments, the composite metallic nanostructures comprise at least two metals selected from gold, silver, copper, platinum, palladium, cadmium, iron, nickel, and zinc. In an exemplary embodiment, the composite metallic nanostructures comprise gold and silver.

In one exemplary embodiment, the first binding partner is linked to gold or a composite nanoparticle and the second binding partner is linked to another composite nanomaterial containing two metals selected from the group consisting of gold, silver, copper, platinum, palladium, cadmium, and zinc. In another exemplary embodiment, the first binding partner is conjugated to nanoparticles containing silver and gold and the second binding partner is conjugated to nanoparticles containing gold and copper.

As described herein, significant signal amplification is achievable in a variety of assays. In certain embodiments, the assays are direct, indirect, sandwich, competitive, and secondary labelling assays. In certain further embodiments, these assays may use extinction, scattering, and/or reflectance measurements to monitor specific binding events.

In certain embodiments, the methods of the present invention are capable of detecting femtogram to nanogram quantities of a target analyte in sample.

As noted above, the present application relates to the use of nanomaterial labeled partners, e.g., antibodies conjugated to composite metallic nanostructures, in solution to determine the binding of specific binding partners in a qualitative or quantitative manner. In some embodiments, the solution comprises one or more of a polysaccharide (e.g., maltodextrin), trehalose, a polymeric material (e.g., PEG), a blocking agent (e.g., bovine serum albumin), and/or sodium chloride. In exemplary embodiments, one or more of the solution components, e.g., maltodextrin, may be provided in lyophilized form, e.g., as a bead or pellet. For instance, one or more of the solution components may be provided as a bead or pellet in a spectrophotometric cuvette or in one or more reaction chambers of an analytical rotor. The bead or pellet may be suspended upon the addition of a liquid, e.g., water, saline solution, a liquid sample, etc. In one embodiment, the solution comprises maltodextrin at a final concentration of about 2% to about 20% weight/volume (wt/vol). In another embodiment, the solution comprises maltodextrin at a final concentration of about 4% to about 15% wt/vol. In yet another embodiment, the solution comprises maltodextrin at a final concentration of about 5% to about 10% wt/vol. In some embodiments, the sensitivity of the assay is improved when maltodextrin is added to the solution when compared to an assay performed in a solution comprising an alternative sugar, e.g., sucrose or ficoll.

In another aspect, the present invention provides analyte detection devices for utilizing the methods described herein to detect a target analyte in a sample. Suitable analyte detection devices may include, but are not limited to, a spectrophotometric cuvette, an analytical rotor, a microwell plate, a clinical analyzer (e.g., Cobas Fara), or a flow chamber. The tip of an optical fiber or a transparent gel may also be employed to carry out the detection methods disclosed herein. In an exemplary embodiment, the analyte detection device is selected from a spectrophotometric cuvette and an analytical rotor.

In a preferred embodiment, components of the analyte detection device are contained within a centrifugal rotor or disc. In some embodiments, a rotor or disc may contain one or more reaction chambers in which the plurality of detection conjugates is located. In certain embodiments, the detection conjugates are present in the form of lyophilized compositions, such as lyophilized beads or pellets. In some embodiments, the analyte detection device comprises a rotor or disc having one or more reaction chambers, wherein each reaction chamber comprises a plurality of detection conjugates (e.g., a first detection conjugate and a second detection conjugate), wherein the detection conjugates are coupled to metallic nanoparticles, e.g., composite metallic nanostructures. In embodiments in which the rotor or disc contains more than one reaction chamber, the detection conjugates can be selected such that a different analyte can be detected in each reaction chamber.

In yet another aspect, the present invention provides kits comprising the analyte detection devices of the invention. In one embodiment, the kit comprises a plurality of detection conjugates (e.g., a first detection conjugate and a second detection conjugate), wherein the detection conjugates are coupled to metallic nanoparticles, e.g., composite metallic nanostructures. In some embodiments, one or more of the detection conjugates may be lyophilized. In one embodiment, all of the detection conjugates are lyophilized. In an exemplary embodiment, the metallic nanostructure in the first detection conjugate and/or the second detection conjugate is a composite metallic nanostructure.

In yet another aspect, the present invention provides a method for preparing composite metallic nanostructures for use in the detection devices and methods described herein. In one embodiment, the methods comprise preparing a first solution comprising a mixture of a polymer and chloroauric acid, preparing a second solution comprising silver or copper nanostructures, and incubating the first solution with the second solution for a period of time, wherein the resulting mixture comprises gold-coated silver nanostructures or gold-coated copper nanostructures. In certain embodiments, a reducing agent, such as ascorbic acid, is added to the reaction mixture to increase the quantity of nanostructures produced. In one embodiment, the polymer in the first solution is polyvinylpyrrolidone. In another embodiment, the polymer in the first solution is polyvinyl alcohol. In another embodiment, the method comprises preparing a first solution comprising a mixture of a detergent such as CHAPS and chloroauric acid, and a solution comprising silver or copper salts, and incubating the first solution with the second solution containing a reducing agent, such as ascorbic acid leading to the formation of composite nanostructures. The size and shape of the nanostructures can be varied by changing the ratio of metals used, concentration of detergent and finally the amount of ascorbic acid used.

BRIEF DESCRIPTION OF THE DRAWINGS

FIG. 6. Illustrates the blue colored colloidal conjugates of chicken anti-protein A react with protein A over a wide concentration range and the reaction rates are linear over extended time.

FIGS. 9A, 9B, and 9C. Illustrates a comparison of TSH detection without PEG (FIG. 9A) or with PEG (FIG. 9B) in the reaction medium. Two monoclonal antibodies (C1 and C6) were used as colloidal gold conjugates. The ratios of the two conjugates were varied and optimal signal was obtained at 30% C1 and 70% C6. FIG. 9C shows the TSH LSPR Peak-Shift comparison of detection with PEG included in the reaction medium. FIG. 9C demonstrates that PEG enhances analyte detection in the TSH assay at 500 seconds.

DETAILED DESCRIPTION OF THE INVENTION

Figure 1:
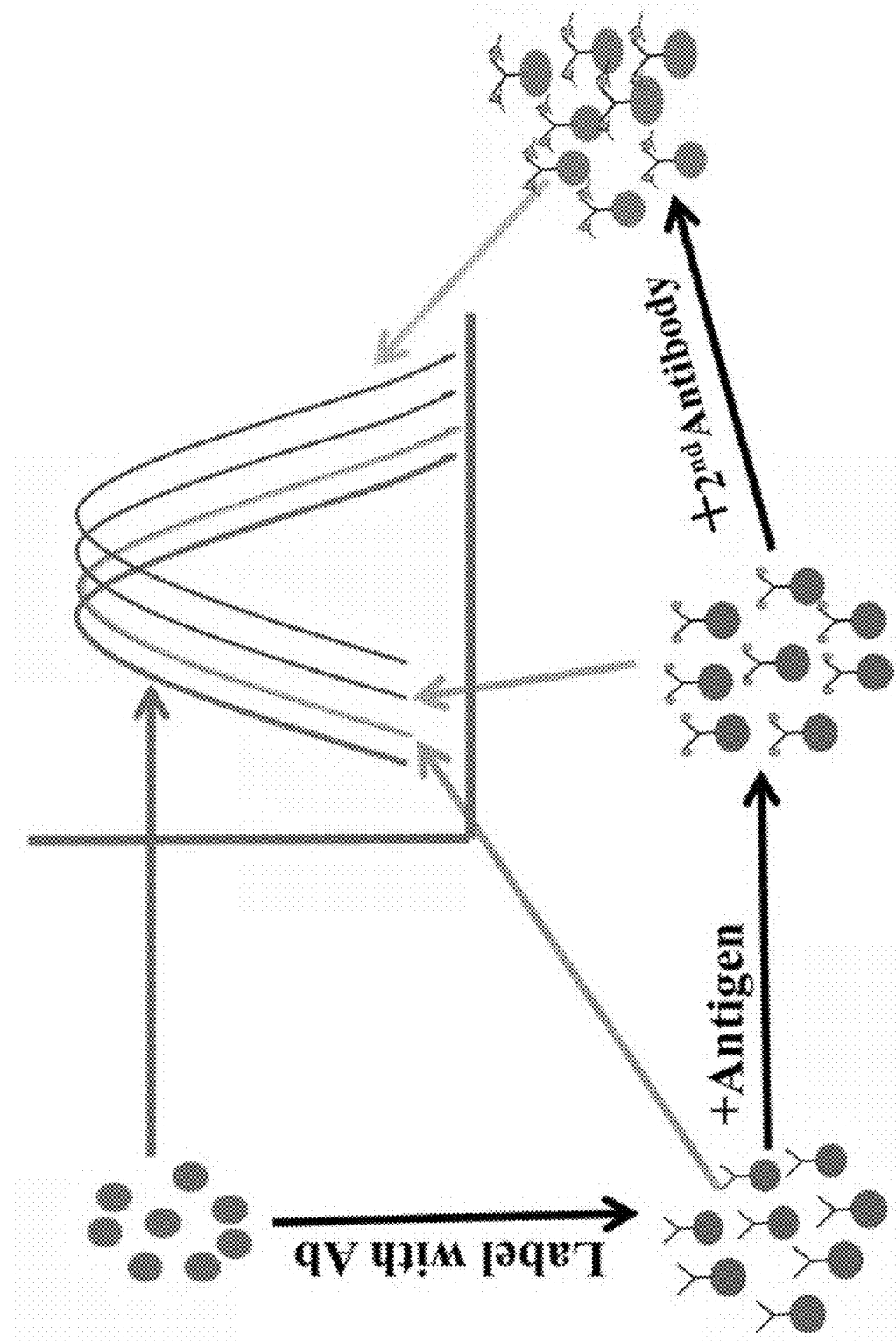
FIG. 1. Illustrates the basic principle of the LSPR immunoassay described herein. The metallic nanoparticle by itself exhibits an optical spectrum that is dependent on the metal composition, size, shape and the nature of the dispersing medium. Slight changes at the surface of the nanoparticle due to first primary binding and subsequent secondary binding cause progressive changes in the characteristics of the light interacting with the nanoconjugates. Such changes can be recorded by a suitable spectrometer and provide qualitative as well as quantitative information.
Figure 2:
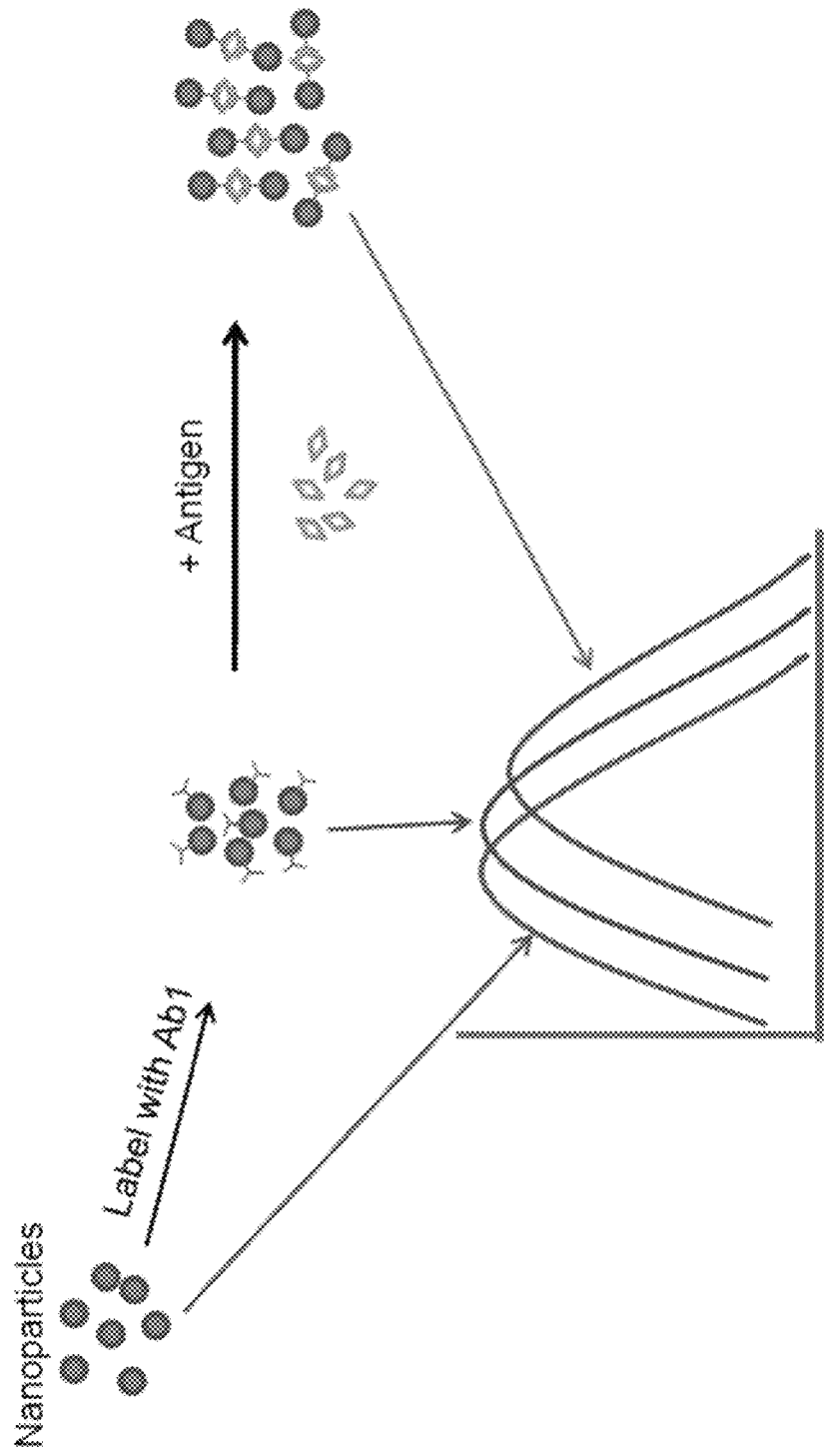
FIG. 2. Illustrates an example in which the receptor has multiple ligand binding sites. Antibodies labelled with nanoparticles cause a spectral shift when bound to antigen.
Figure 3:
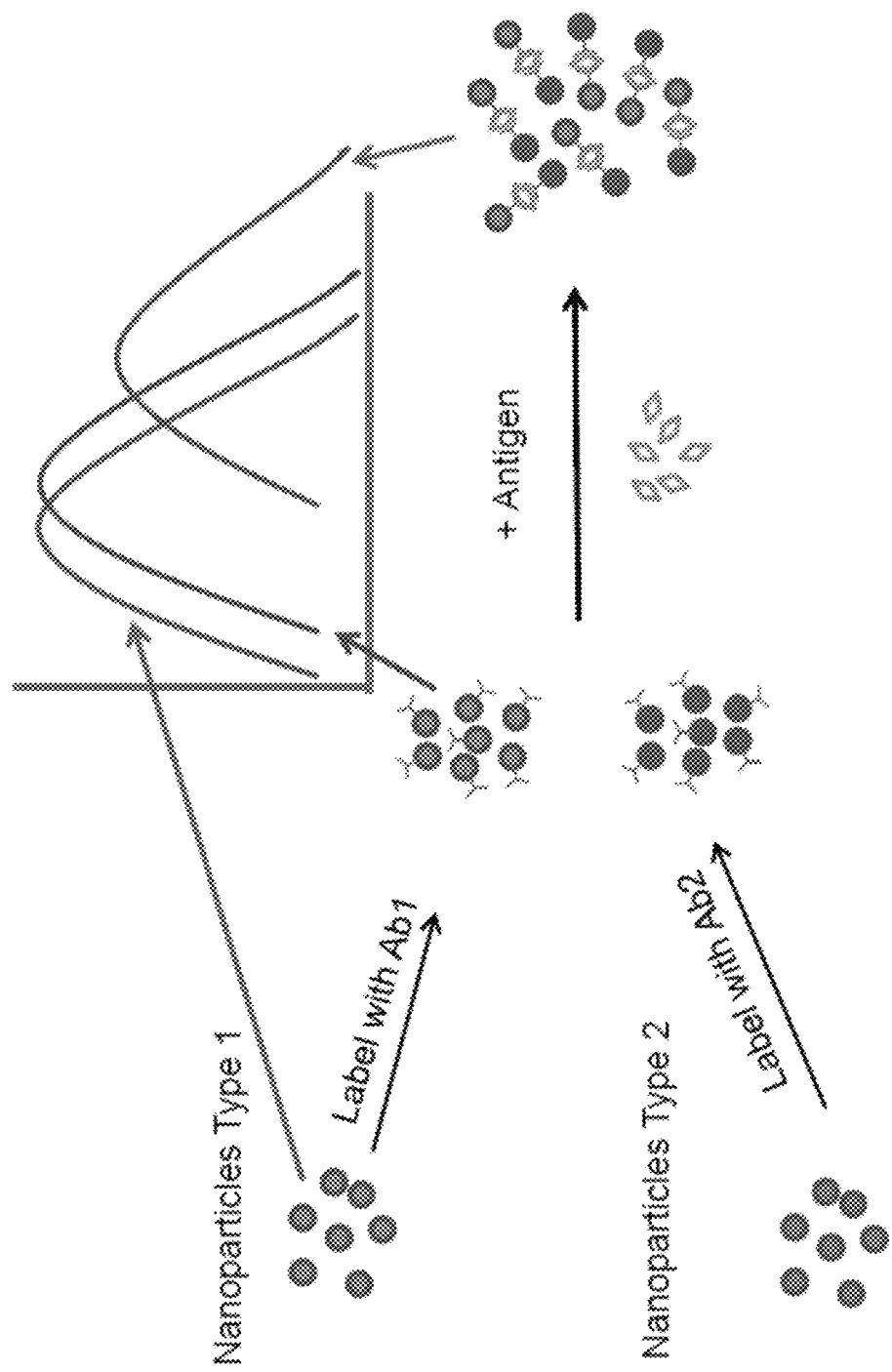
FIG. 3. Illustrates the LSPR coupling effect between different nanoparticle types when the receptor has multiple binding sites or the receptor has different binding sites.
Figure 4:
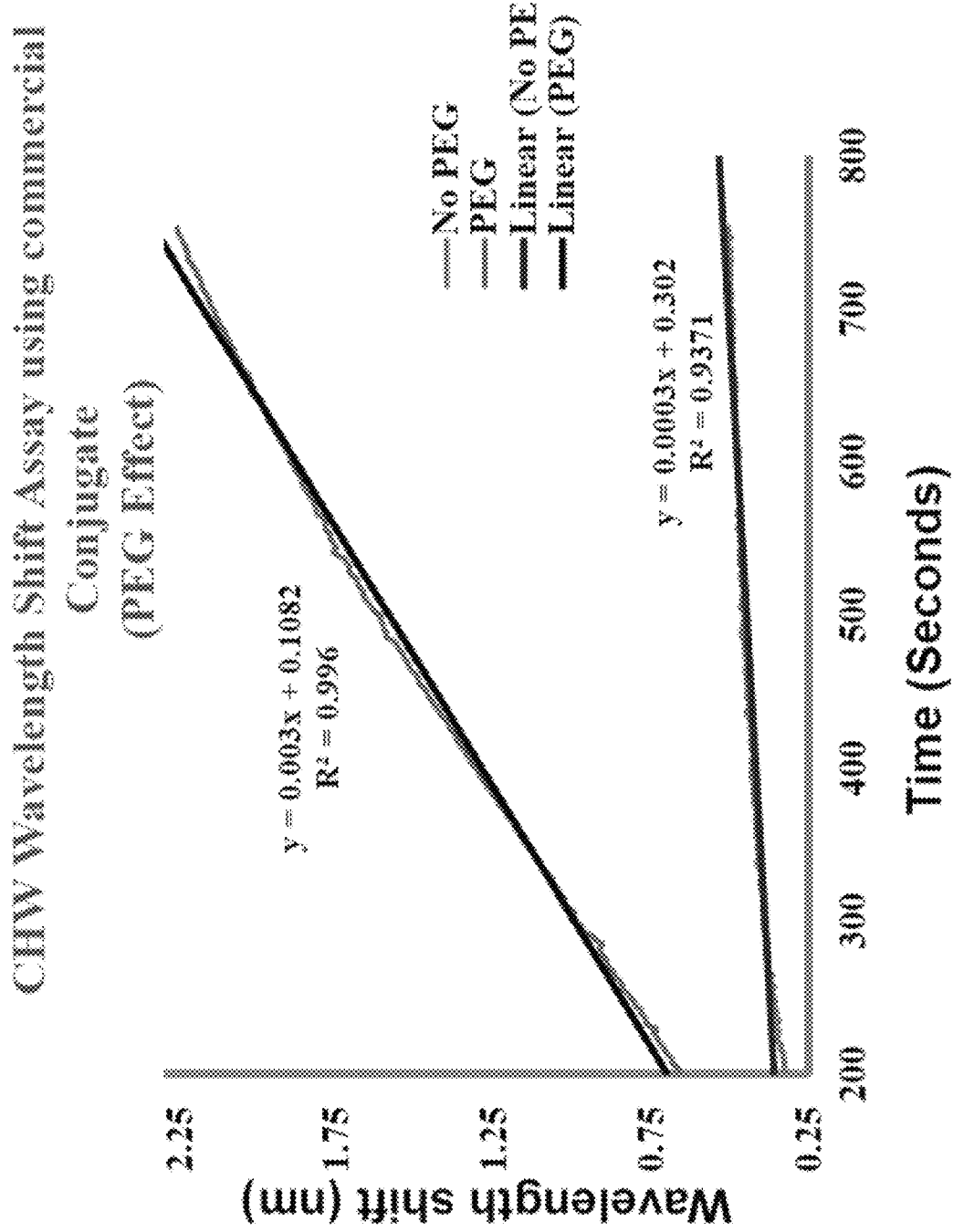
FIG. 4. Illustrates the effect of polyethylene glycol (PEG) on LSPR signals. The LSPR signals are substantially increased in the presence of PEG. This figure shows a ten-fold enhancement in the LSPR signal upon addition of PEG to the reaction medium containing 2.5 ng heartworm antigen and anti-heartworm polyclonal antibody.
Figure 5:
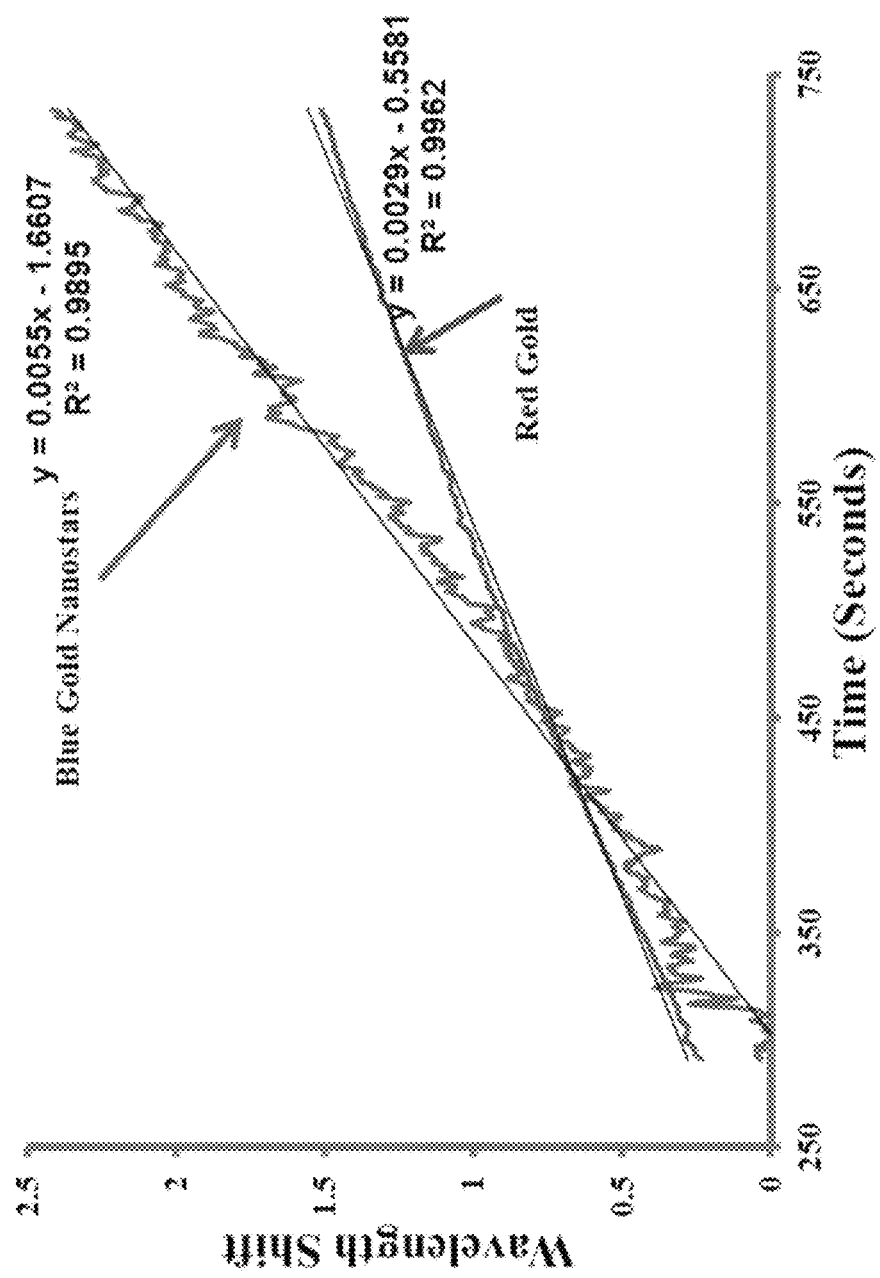
FIG. 5. Illustrates the increase in wavelength shift by utilizing blue colored gold nanostars. In this figure, antibody conjugated to blue colored nanostars provided a 2-fold increase in the rate of wavelength shift when compared with red colloidal gold conjugate of the antibody. This experiment was set up using 2.5 ng of crude heartworm extract as antigen and then reacted either with a commercial conjugate prepared using red colloidal gold or novel blue conjugate prepared per this invention. Polyethylene glycol was used in both types of conjugates.
Figure 7A:
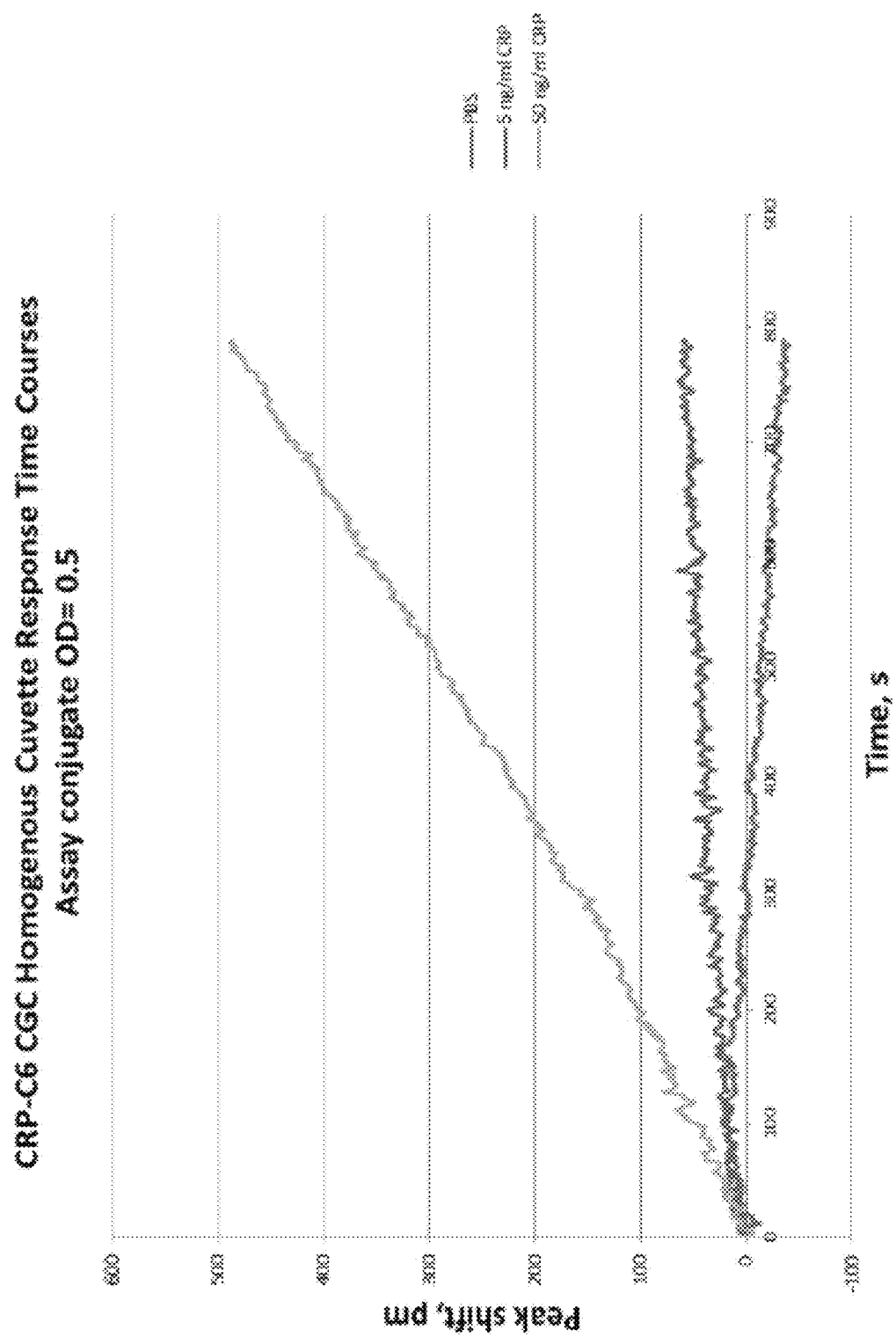
FIGS. 7A and 7B. Illustrates a substantial improvement in analyte detection when the LSPR technique is used in solution phase (FIG. 7A) rather than the solid phase (FIG. 7B). The reactions were performed either in the solid phase using a Nicoya chip or in liquid phase using a Nicoya cuvette assembly. The same Nicoya spectrometer was used in the two experiments. The CRP responses in the cuvette assay (solution phase) were approximately 6- to 8-fold greater than in the solid phase.
Figure 7B:
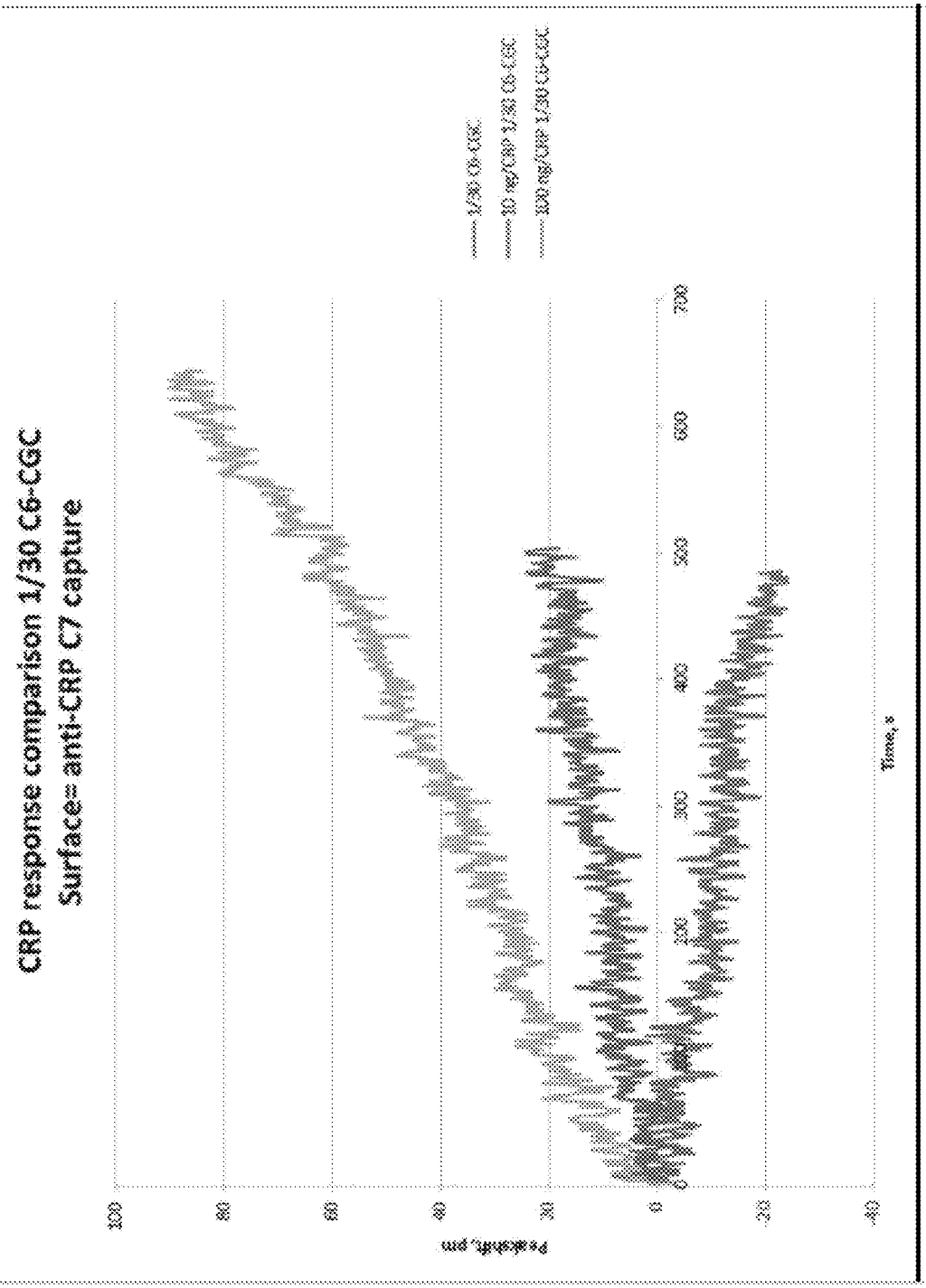
Figure 8A:
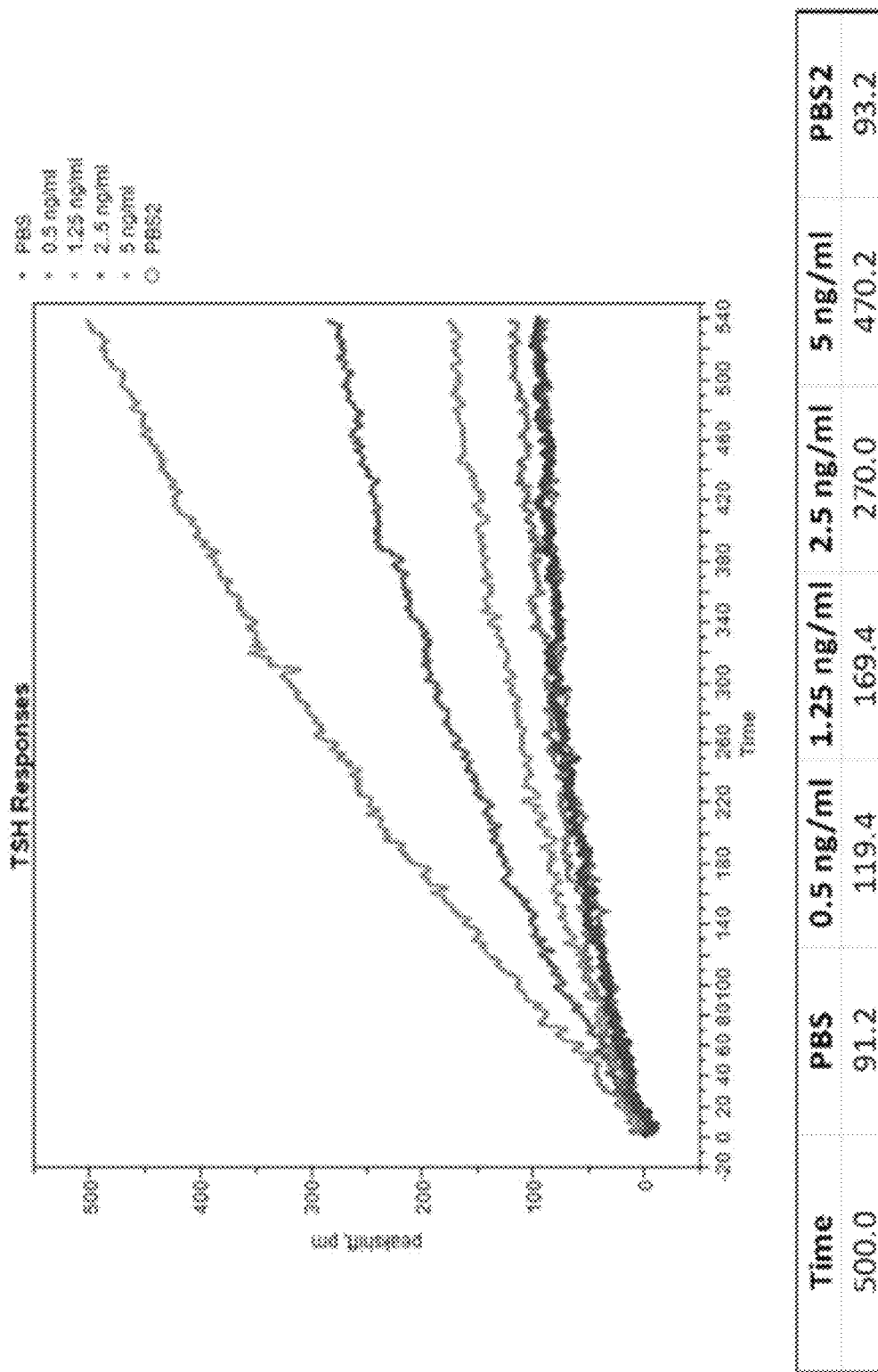
FIGS. 8A and 8B. Illustrates the detection of TSH in solution phase using colloidal gold conjugated monoclonal anti-TSH antibodies.
Figure 8B:
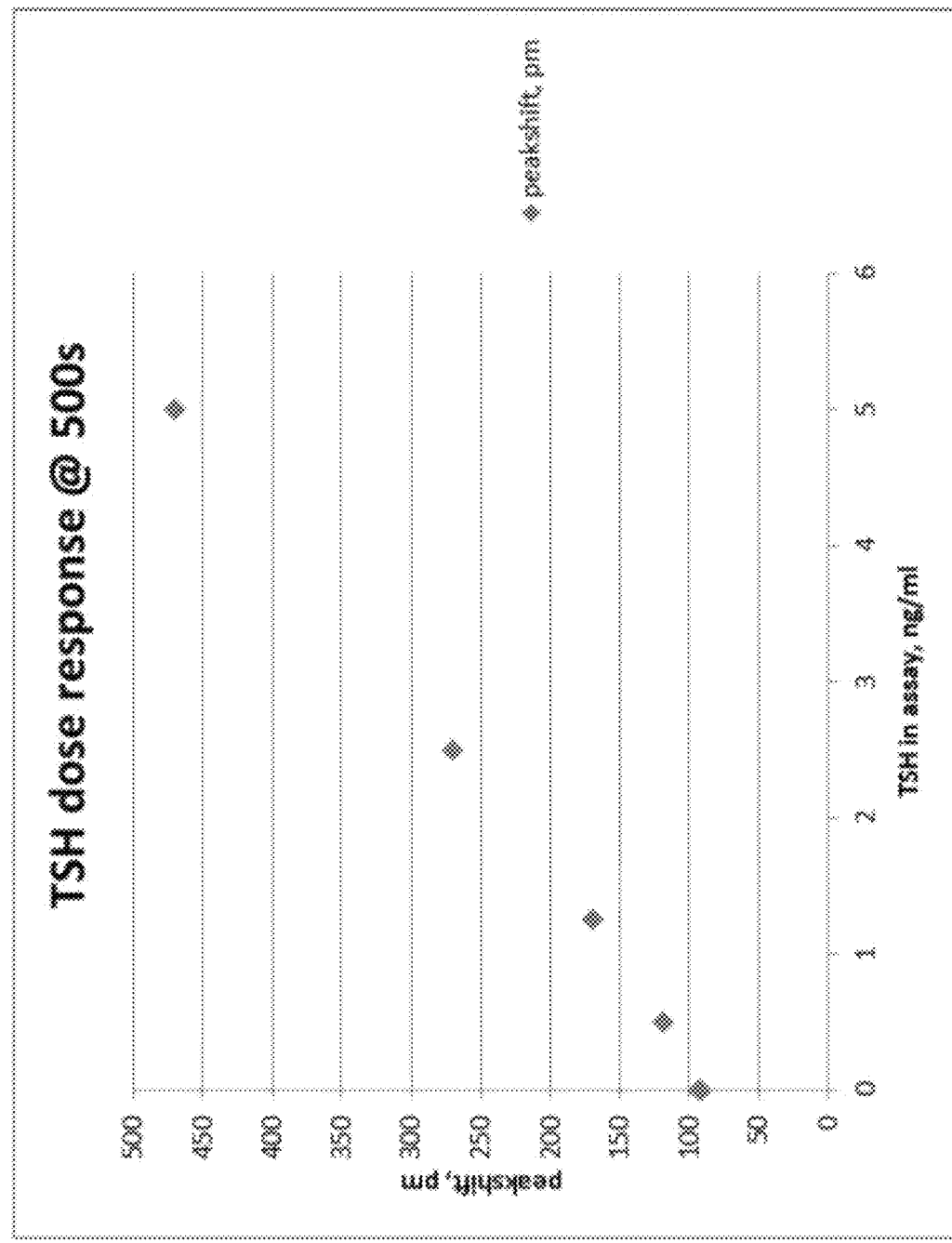
Figure 9A:
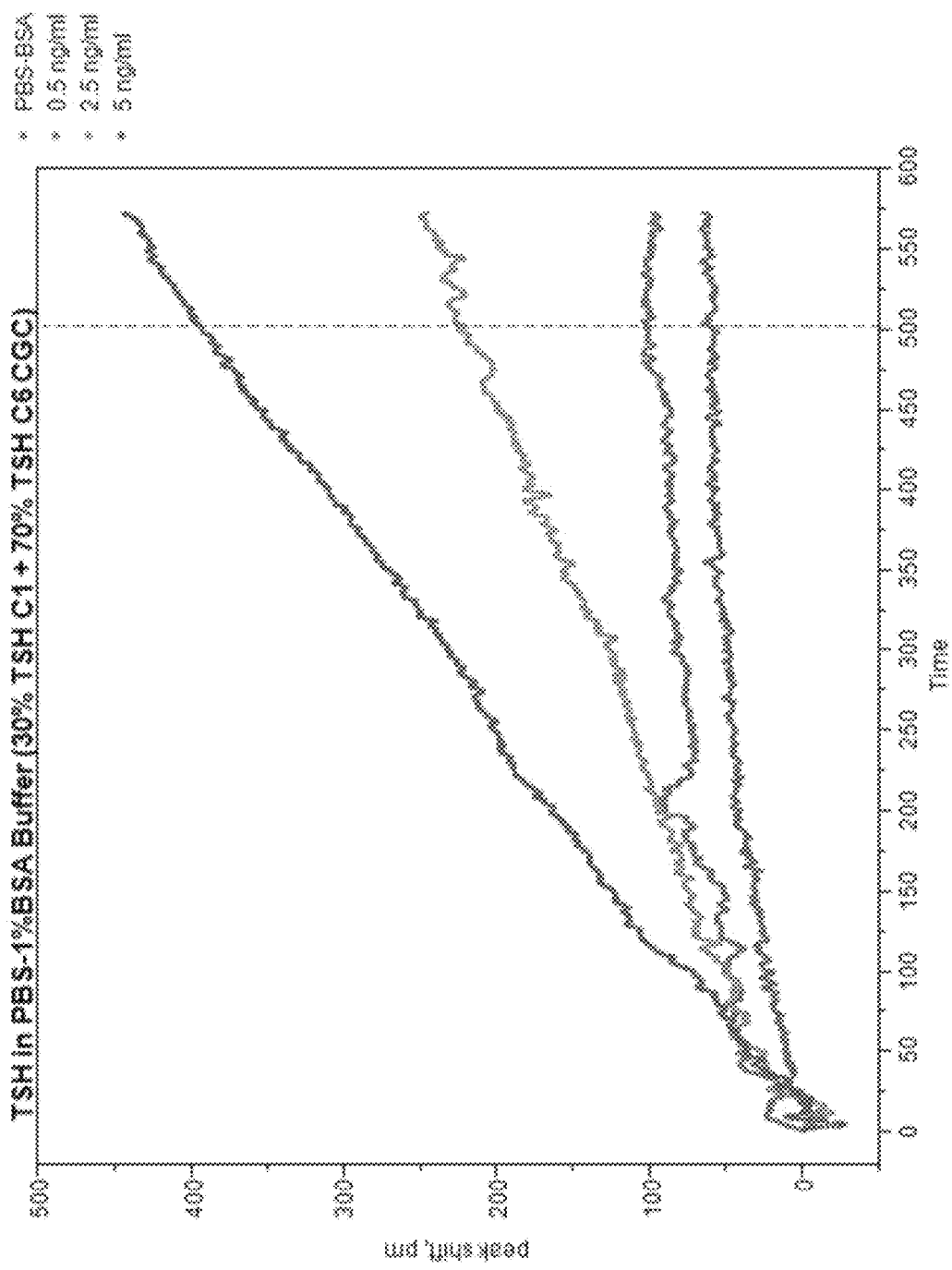
Figure 9B:
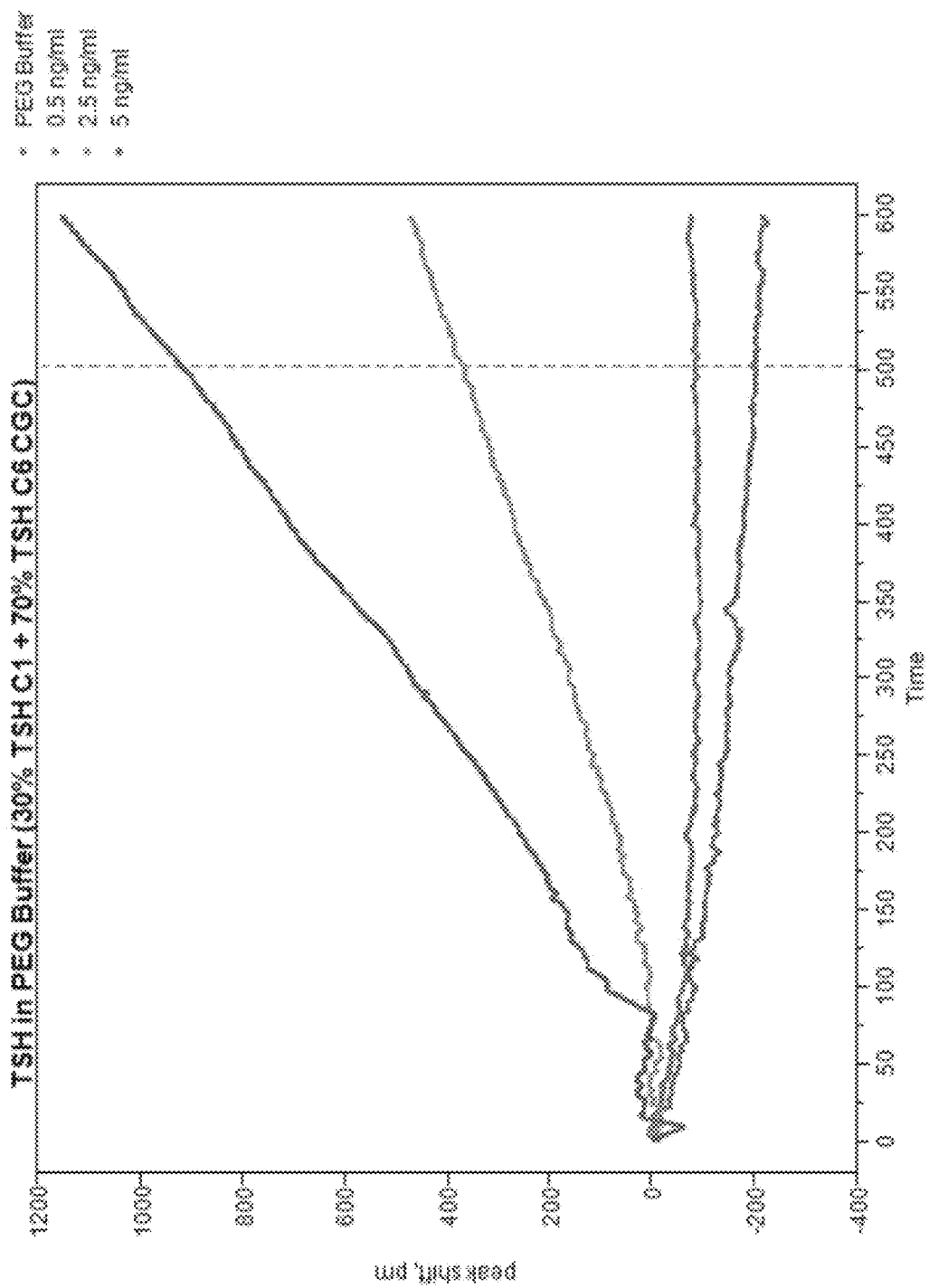

The present invention is based, in part, on the discovery that significant amplification in LSPR-based assays can be achieved with composite metallic nanostructure-labeled binding partners. Thus, the present invention provides analyte detection methods utilizing a plurality of detection conjugates comprising composite metallic nanostructures coupled to biomolecules.

The present invention overcomes problems of current immunoassays, ligand-receptor binding assays, nucleic acid-protein binding assays or other specific binding partner assays that generally require multiple steps and sophisticated equipment to perform such steps. The lack of sensitivity and the complexity involved in performing such heterogeneous assays arises from the specific need to separate labeled from unlabeled specific binding partners. The present invention overcomes such limitations by performing all steps involved in the assay in a homogenous format wherein the separation of reacted and unreacted assay components is unnecessary as the binding events change LSPR characteristics that are measured in real time by any of the spectroscopic techniques used by those of ordinary skill in spectroscopy. Separation free, one pot assays of the present invention use plasmonic coupling and related effects to provide amplification of the final LSPR modulated signals.

As will be apparent to one of ordinary skill in the art, the present invention may be applied to the detection of a variety of antigenic analytes, such as those associated with infectious diseases in both humans and animals, e.g., antigens associated with infectious diseases and antibodies generated in response thereto. Beyond the detection of antigens and antibodies, the techniques described herein may also be used for performing assays involving specific binding partners such as ligands and receptors, and transcription factors and their associated DNA binding elements. Moreover, RNA-RNA, RNA-DNA, DNA-DNA or protein-nucleic acid interactions may be detected using appropriate conjugates of metallic nanoparticles with specific binding partners.

As provided herein, the present invention describes the use of metallic nanoparticles in solution (as opposed to being attached to a surface via chemical or physical deposition) to determine the binding of specific binding partners in a qualitative or quantitative manner. The changes in the characteristics of light interacting with the regions containing unbound and bound partners attached to metallic nanoparticles can be measured, allowing for both qualitative and quantitative interactions between the specific binding partners to be determined by suitable detectors.

In a first aspect, the present application provides methods of detecting a target analyte in a sample. In some embodiments, the methods comprise mixing the sample with a plurality of detection conjugates that comprise metallic nanostructures coupled to binding partners. In one embodiment, the methods comprise a first detection conjugate and a second detection conjugate, wherein the first and second detection conjugates comprise metallic nanostructures coupled to binding partners that are capable of specifically binding to the target analyte if present in the sample to form a complex between the first detection conjugate, the analyte, and the second detection conjugate; exposing the complex to a light source at a wavelength range within the ultraviolet-visible-infrared spectrum; and measuring an optical signal from the complex, wherein a change in the optical signal indicates the presence of the target analyte in the sample. In an exemplary embodiment, the metallic nanostructure in the first detection conjugate and/or the second detection conjugate is a composite metallic nanostructure. In another exemplary embodiment, the step of mixing occurs in the presence of a polymeric material selected from polyethylene glycol (PEG), polyvinylpyrrolidone, polyallylamine, polyethyleneimine, polylysine, polyacrylic acid, polyvinylalcohol, and polyaspartic acid. In a preferred embodiment, the polymeric material is PEG. In yet another exemplary embodiment, the step of mixing occurs in the presence of a polysaccharide. In some embodiment, the polysaccharide is selected from maltodextrin, corn syrup, and polyglucose. In a preferred embodiment, the polysaccharide is maltodextrin. In yet another exemplary embodiment, the step of mixing occurs in the presence of a blocking agent. In some embodiments, the blocking agent is selected from bovine serum albumin, casein, gelatin, ovalbumin, and gamma-globulins. In a preferred embodiment, the blocking agent is bovine serum albumin.

In various embodiments described herein, the methods of the present invention can be configured in a sandwich assay format, a direct assay format, an indirect assay format, as well competitive and secondary labelling formats.

In some embodiments, the detection methods are sandwich assays. In such embodiments, the detection conjugates comprise metallic nanostructures coupled to binding partners that are capable of specifically binding to the target analyte if present in the sample. For instance, in one embodiment, the method in a sandwich assay format comprises a first detection conjugate and a second detection conjugate wherein the first and second detection conjugates comprise metallic nanostructures coupled to binding partners that are capable of specifically binding to the target analyte if present in the sample to form a complex between the first detection conjugate, the analyte, and the second detection conjugate. In an exemplary embodiment, the metallic nanostructure in the first detection conjugate and/or the second detection conjugate is a composite metallic nanostructure. The complex is exposed to a light source and an optical signal is measured, wherein a change in the optical signal indicates the presence of analyte in the sample. By way of illustration, when a sample containing the target analyte is mixed with the first and second detection conjugates, the target analyte binds to the binding partners in the detection conjugates to form a complex between the first detection conjugate, the analyte, and the second detection conjugate. This complex formation brings the metallic nanostructures in the detection conjugates in close proximity to each other, i.e., plasmon-plasmon coupling. The amount of light that is absorbed, scattered, or transmitted by the metallic nanostructures is affected by the proximity of the metallic nanostructures in the complex and thus produces an enhanced shift in the peak absorption wavelength, which indicates the presence of the target analyte in the sample.

In other embodiments, the detection methods are competitive assays. In such embodiments, the first detection conjugate comprises metallic nanostructures coupled to the target analyte of interest. As in the sandwich assay method, the second detection conjugate is capable of specifically binding to the target analyte. In this type of assay, the first detection conjugate will bind to the second detection conjugate initially. If a sample containing a target analyte is mixed with these initial complexes, the unlabeled or free target analyte in the sample will compete with the first detection conjugate for binding to the second detection conjugate. The change in optical signal in this type of assay will result from the displacement of the metallic nanostructures in the first detection conjugate from the second detection conjugate, which will proportionately reduce the wavelength shift in the peak absorption wavelength.

As noted above, the methods of the invention may utilize a plurality of detection conjugates. Detection conjugates comprise metallic nanostructures coupled to binding partners capable of specifically binding to a target analyte or another detection conjugate depending on the assay configuration. For example, in embodiments in which the method is configured in a sandwich assay format, the detection conjugates comprise metallic nanostructures coupled or conjugated to binding partners that are capable of specifically binding a target analyte. In other embodiments in which the method is configured in a direct competitive assay format, at least one of the detection conjugates comprises metallic nanostructures coupled or conjugated to target analytes. In an exemplary embodiment, the metallic nanostructure in the first detection conjugate and/or the second detection conjugate is a composite metallic nanostructure.

In some embodiments, the detection conjugates comprise binding partners that are capable of specifically binding to a target analyte. As used herein, "specific binding" refers to binding to a target molecule with high affinity, e.g., an affinity of at least $10^{-6}$ M. In some embodiments, the binding partners are haptens and other small molecules, drugs, hormones, biological macromolecules including, but not limited to, antibodies or fragments thereof (e.g., Fv, Fab, (Fab)$_2$, single chain, CDR etc.), antigens, receptors, ligands, polynucleotides, aptamers, polypeptides, polysaccharides, lipopolysaccharides, glycopeptides, lipoproteins, or nucleoproteins. In certain embodiments, the binding partners are antibodies. In other embodiments, the binding partners are antigens.

In some embodiments, the detection conjugates, e.g., a first detection conjugate and a second detection conjugate, comprise binding partners that are the same type of molecule, but preferably bind to the target analyte at locations distinct from the other. By way of example, a first detection conjugate and a second detection conjugate can both be antibodies that recognize a target analyte, but the epitope to which the first detection conjugate binds the target analyte is separate from and ideally non-overlapping with the epitope to which the second detection conjugate binds the target analyte. Thus, in certain embodiments, the first detection conjugate comprises an antibody that recognizes a first epitope of a target analyte and the second detection conjugate comprises a different antibody that recognizes a second epitope of a target analyte. In various embodiments described herein, the first detection conjugate may comprise a monoclonal antibody that recognizes a first epitope of a target analyte. In further embodiments, the second detection conjugate may comprise a monoclonal antibody that recognizes a second epitope of a target analyte that is separate from and ideally non-overlapping with the epitope that is recognized by the first detection conjugate. Alternatively, the first detection conjugate and/or the second detection conjugate may comprise a polyclonal antibody. For instance, the first detection conjugate may comprise a polyclonal antibody while the second detection conjugate comprises a monoclonal antibody. In some embodiments, the first detection conjugate comprises a polyclonal antibody and the second detection conjugate comprises a polyclonal antibody.

The metallic nanostructures in the detection conjugates can be composed of a noble metal or composite thereof. In some embodiments, the metallic nanostructures in the detection conjugates may be composed of a transition metal or composite thereof. In some embodiments, the metallic nanostructures in the detection conjugates may comprise an alkali metal or lanthanide in combination with a noble or transition metal. In certain embodiments, metallic nanostructures in the detection conjugates comprise a metal selected from gold, silver, copper, platinum, palladium, ruthenium, rhodium, osmium, iridium, titanium, chromium, cadmium, zinc, iron, cobalt, nickel, and composites thereof. In one embodiment, the metallic nanostructures are gold nanostructures. In another embodiment, the metallic nanostructures are silver nanostructures.

In preferred embodiments, the metallic nanostructures in the detection conjugates are composite metallic nanostructures. "Composite metallic nanostructures" refers to nanostructures that comprise at least two noble metals, transition metals, alkali metals, or lanthanides. The two or more metals may be mixed together, as in an alloy, or the two or more metals may be present in separate portions of the nanostructure. For example, one metal may form the core of the nanostructure, whereas the second metal forms an outer shell or coating of the nanostructure. In some embodiments, the composite metallic nanostructures comprise at least two metals selected from gold, silver, copper, platinum, palladium, ruthenium, rhodium, osmium, iridium, titanium, chromium, cadmium, zinc, iron, cobalt, and nickel. In other embodiments, the composite metallic nanostructures comprise at least two metals selected from gold, silver, copper, platinum, palladium, cadmium, iron, nickel, and zinc. In one particular embodiment, the composite metallic nanostructures comprise gold and silver. In another embodiment, the composite metallic nanostructures comprise gold and copper. In yet another embodiment, the composite metallic nanostructures comprise silver and copper. The composite metallic nanostructures used in the methods of the invention can include a number of different geometries, such as spherical nanoparticles, pyramidal nanoparticles, hexagonal nanoparticles, nanotubes, nanostars, nanoshells, nanorods, nanodots, nanoislands, nanowires, nanodisks, nanocubes, or combinations thereof. In an exemplary embodiment, the composite metallic nanostructure is selected from a nanostar and a nanorod.

In certain embodiments, the composite metallic nanostructures used in the methods of the invention are alloys of a first metal and a second metal. In some embodiments, the composite metallic nanostructures used in the methods of the invention comprise a core of a first metal and a coating of a second metal. In particular embodiments, the composite metallic nanostructures comprise a silver core and a gold coating. In other embodiments, the composite metallic nanostructures comprise a copper core and a gold coating. In another embodiment, the core is silver and the coating is copper. In some embodiments, each of the composite metallic nanostructures comprises a dielectric core (e.g. silicon dioxide, gold sulfide, titanium dioxide, silica, and polystyrene), a first coating of a first metal, and a second coating of a second metal. In one particular embodiment of the detection methods, the core is silica, the first coating (i.e. inner coating) is a silver coating, and the second coating is a gold coating (i.e. outer coating). In another embodiment, the core is silica, the first coating (i.e. inner coating) is a copper coating, and the second coating is a gold coating (i.e. outer coating).

In some embodiments, the core comprising a first metal is dissolved following the coating process with a second metal to create a hollow structure comprised of the second metal. For instance, coating of a silver core with gold nanoparticles generates a gold shell around the silver core and the silver core is subsequently dissolved or degraded resulting in the formation of a hollow nanogold shell structure.

The metallic nanostructures include spherical nanoparticles as well nanoplates and nanoshells. Nanoplates have lateral dimensions (e.g. edge lengths) that are greater than their thickness. Nanoplates include nanodisks, nanopolygons, nanohexagons, nanocubes, nanorings, nanostars, and nanoprisms. In some embodiments, the metallic nanostructures, including the composite nanostructures, have a geometry selected from spherical nanoparticles, pyramidal nanoparticles, hexagonal nanoparticles, nanotubes, nanostars, nanoshells, nanorods, nanodots, nanoislands, nanowires, nanodisks, nanocubes, or combinations thereof. Other shapes are also possible, including irregular shapes. In certain embodiments, the size and shape of the metallic nanostructures are not uniform—i.e. the metallic nanostructures are a heterogeneous mixture of different shapes and sizes of nanostructures. In an exemplary embodiment, the metallic nanostructures are nanostars. In another exemplary embodiment, the metallic nanostructures are nanorods. In another exemplary embodiment, the metallic nanostructures are composite nanospheres.

For spherical nanoparticles, suitable diameter ranges include from about 5 nm to about 200 nm, from about 10 nm to about 100 nm, and from about 20 nm to about 60 nm. For nanorods, suitable diameter ranges include from about 5 nm to about 50 nm, from about from about 8 nm to about 30 nm, and from about 10 nm to about 25 nm. Furthermore, for nanorods, suitable length ranges include from about 25 nm to about 150 nm, from about 40 nm to about 120 nm, and from about 50 nm to 100 nm. In some embodiments, the aspect ratio, i.e., length/diameter, of the nanorods is between 2 and 10. For nanoplates, edge lengths may be from about 10 nm to about 800 nm, from about 20 nm to about 500 nm, from about to 50 nm to about 200 nm, from about 30 nm to about 100 nm, or from about 10 nm to about 300 nm. The thickness of the nanoplates can range from about 1 to about 100 nm, from about 5 nm to about 80 nm, from about 10 nm to about 50 nm, or from about 5 nm to about 20 nm.

In some embodiments, the nanoplates have an aspect ratio greater than 2. The aspect ratio is the ratio of the edge length to the thickness. Preferably, the nanoplates have an aspect ratio from about 2 to about 25, from about 3 to about 20, from about 5 to about 10, from about 2 to about 15, or from about 10 to about 30.

Methods of conjugating molecules to metallic nanostructures are known to those of skill in the art. Such methods include conjugation chemistries, such as those involving 1-Ethyl-3-[3-dimethylaminopropyl]carbodiimide hydrochloride (EDC), sulfo-NHS coupling, hydrophobic binding or thioether chemistry. In some embodiments, the binding partners or target analytes can be coupled to the metallic nanostructures through various chemical functionalities including thiol, amine, dithiol, acrylic phosphoramidite, azide, or alkynes. In some embodiments, the molecule can be coupled to the metallic nanostructure indirectly through a larger carrier molecule or protein. Such indirect coupling is particularly useful when the molecule is small, such as a hormone, a drug, and other small molecules less than 10 kD. Preferably, the carrier protein is not capable of specific interaction with the target analyte. In some embodiments, protein A or protein G or protein A/G may be conjugated or coupled to the nanoparticles.

In some embodiments, the metal or metals employed in a first detection conjugate can be the same as the metal or metals from which the metallic nanostructures in the second detection conjugate are fabricated. For example, in one embodiment, the first detection conjugate comprises gold nanostructures and the second detection conjugate comprise gold nanostructures. In other embodiments, the metal employed in the first detection conjugate is different from the metal or metals used to create the metallic nanostructures in the second detection conjugate. For instance, in some embodiments, the first detection conjugate comprises silver nanostructures and the second detection conjugate comprises gold nanostructures. In other embodiments, the first detection conjugate comprises gold nanostructures and the second detection conjugate comprises silver nanostructures. In certain embodiments, the first detection conjugate comprises gold nanostructures and the second detection conjugate comprises composite nanostructures. In related embodiments, the composite nanostructures comprise gold-coated silver nanostructures. In other particular embodiments, the first detection conjugate comprises gold nanostructures and the second detection conjugate comprises composite nanostructures comprising gold-coated copper nanostructures. In yet other embodiments, the first detection conjugate comprises gold nanostructures and the second detection conjugate comprises composite nanostructures comprising gold-coated magnetite nanostructures. In still other embodiments, the first detection conjugate comprises gold nanostructures and the second detection conjugate comprises composite nanostructures comprising gold and an alkali metal or lanthanide.

In certain embodiments, the size of the metallic nanostructures used to create the first detection conjugate are similar to the size of the metallic nanostructures used in the second detection conjugate. In such embodiments, matching the size of the two sets of nanostructures can provide an optimal wavelength shift in a reflectance, emission or scattering spectrum.

In some embodiments, the reaction environment may be adjusted with appropriate buffers, ionic strength, and other accelerants. In a preferred embodiment, the reaction environment comprises polyethylene glycol (PEG), which, as described herein, can enhance the strength of the LSPR signal. Other similar polymeric materials may also be used, including, but not limited to, polyvinylpyrrolidone, polyallylamine, polyethyleneimine, polylysine, polyacrylic acid, polyvinylalcohol, and polyaspartic acid.

The present invention also provides analyte detection devices for utilizing the methods described herein to detect a target analyte in a sample. Suitable analyte detection devices may include, but are not limited to, a spectrophotometric cuvette, an analytical rotor, a microwell plate, or a flow chamber. As will be understood by the skilled artisan, the tip of an optical fiber or a transparent gel may also be employed to carry out the detection methods disclosed herein.

In certain embodiments, all components of the analyte detection devices described herein are contained within a centrifugal rotor or disc. For instance, a rotor or disc may contain one or more reaction chambers in which the plurality of detection conjugates is located. In some embodiments, the detection conjugates are present in the form of lyophilized compositions, such as lyophilized beads or pellets. In some embodiments, the analyte detection device comprises a rotor or disc having one or more reaction chambers, wherein each reaction chamber comprises a plurality of detection conjugates (e.g., a first detection conjugate and a second detection conjugate), wherein the detection conjugates are coupled to metallic nanoparticles. Such a device provides a one-step analyte detection assay whereby a test sample is contacted with the rotor or disc, and application of a centrifugal force to the rotor or disc delivers the test sample to the reaction chambers where the sample mixes with the first detection conjugate and the second detection conjugate. In embodiments in which the rotor or disc contains more than one reaction chamber, the detection conjugates can be selected such that a different analyte can be detected in each reaction chamber. These rotor-format detection devices can be configured in the sandwich assay format, the direct competitive format, or both if the rotors comprise multiple reaction chambers.

Any of the types of metallic nanostructures discussed herein can be used with these rotor-format detection devices. In some embodiments, the first detection conjugate comprises gold nanostructures and the metallic nanostructures in the second detection conjugate are gold nanostructures. In other embodiments, the first detection conjugate comprises silver nanostructures and the metallic nanostructures in the second detection conjugate are gold nanostructures. In still other embodiments, the first detection conjugate comprises gold nanostructures and the second detection conjugate comprises composite nanostructures. For instance, in one embodiment, the composite nanostructures are gold-coated silver nanostructures. In another embodiment, the composite nanostructures are gold-coated copper nanostructures.

The present invention also includes kits comprising the analyte detection devices of the invention as disclosed herein. In one embodiment, the kit comprises a plurality of detection conjugates (e.g., a first detection conjugate and a second detection conjugate), wherein the detection conjugates are coupled to metallic nanoparticles. In some embodiments, one or more of the detection conjugates may be lyophilized, for example, in the form of a pellet or bead. In one embodiment, all of the detection conjugates are lyophilized. In further embodiments, the kit may include one or more additional reagents. In some embodiments, one or more of the additional reagents is provided in lyophilized form. In some embodiments, the kit may comprise a blocking agent, a sugar, a polymeric accelerant material, sodium chloride, and/or combinations thereof. A "blocking agent" is an agent that prevents the association of proteins present in the sample with the detectable agent and/or analyte. Blocking agents are typically proteins themselves and may include, but are not limited to, bovine serum albumin, casein, gelatin, ovalbumin, gamma-globulins, and. IgG from non-immunized animals. In some embodiments, the sugar is a polysaccharide. In one embodiment, the polysaccharide is selected from maltodextrin, corn syrup, and polyglucose. In a preferred embodiment, the polysaccharide is maltodextrin. In another embodiment, the sugar is trehalose. In some embodiments, the reagent kit may comprise maltodextrin and trehalose. In some embodiments, the polymeric accelerant material is PEG.

The kits of the invention may also include instructions for using the device to detect an analyte in a test sample, devices or tools for collecting biological samples, and/or extraction buffers for obtaining samples from solid materials, such as soil, food, and biological tissues.

As described herein, a test sample can be any type of liquid sample, including biological samples or extracts prepared from environmental or food samples. In one particular embodiment, the test sample is a biological sample. Biological samples include, but are not limited to, whole blood, plasma, serum, saliva, urine, pleural effusion, sweat, bile, cerebrospinal fluid, fecal material, vaginal fluids, sperm, ocular lens fluid, mucous, synovial fluid, peritoneal fluid, amniotic fluid, biopsy tissues, saliva, and cellular lysates. The biological sample can be obtained from a human subject or animal subject suspected of having a disease condition, such as cancer, infectious diseases (e.g., viral-, bacterial-, parasitic- or fungal-infections), cardiovascular disease, metabolic disease, autoimmune disease etc. The biological sample can also be obtained from a healthy subject (e.g. human or animal) undergoing a routine medical check-up.

In some embodiments of the methods, the test sample is mixed with a first detection conjugate and the mixture is subsequently brought into contact with the second detection conjugate. In certain embodiments, the sample, the first detection conjugate, and the second detection conjugate are brought into contact at the same time. For instance, contact of the sample with both reagents simultaneously may occur in the rotor-format detection devices described herein.

As noted above, the present application relates to the use of composite nanomaterial labeled partners in solution to determine the binding of specific binding partners in a qualitative or quantitative manner. The present inventors have surprisingly found that the sensitivity of the solution-based assay is significantly enhanced when a polysaccharide, e.g., maltodextrin, is added to the solution as compared with the addition of other sugars such as sucrose, trehalose, or ficoll. In a centrifugal rotor-format, low speed centrifugation is required to deliver a sample into an analytical chamber. The addition of a polysaccharide, e.g., maltodextrin, to the solution is particularly effective in preventing aggregation and sedimentation of the composite nanomaterial labeled partners, e.g., antibodies conjugated to gold-silver nanostars, during and after centrifugation. The improvement in sensitivity in relation to other sugars such as sucrose, trehalose, or ficoll was unexpected. By virtue of the reduced aggregation and sedimentation, increased sensitivity of the assay is achieved. Accordingly, in some embodiments, the methods of the present invention are performed in a solution comprising a polysaccharide, e.g., maltodextrin, corn syrup, or polyglucose.

In one embodiment, the solution comprises a polysaccharide at a final concentration of about 2% to about 20% wt/vol. In another embodiment, the solution comprises a polysaccharide at a final concentration of about 4% to about 15% wt/vol. In yet another embodiment, the solution comprises a polysaccharide at a final concentration of about 5% to about 10% wt/vol. In an exemplary embodiment, the solution comprises a polysaccharide at a final concentration of about 5%, 6%, 7%, 8%, 9%, or 10%, inclusive of all values therebetween. In various embodiments described herein, the sensitivity of the assay may be improved when a polysaccharide is added to the solution as compared to an assay performed in a solution comprising an alternative sugar, e.g., sucrose or ficoll. In an exemplary embodiment, the polysaccharide is maltodextrin.

In one embodiment, the solution comprises a blocking agent at a final concentration of about 0.1% to about 20% wt/vol. In another embodiment, the solution comprises a blocking agent at a final concentration of about 0.5% to about 10% wt/vol. In yet another embodiment, the solution comprises a blocking agent at a final concentration of about 1% to about 5% wt/vol. In an exemplary embodiment, the solution comprises a blocking agent at a final concentration of about 1%, 2%, 3%, 4%, or 5%, inclusive of all values therebetween. In various embodiments described herein, the sensitivity of the assay may be improved when a blocking agent is added to the solution as compared to an assay performed in the absence of a blocking agent. In some embodiments, the blocking agent is selected from bovine serum albumin, casein, gelatin, ovalbumin, and gamma-globulins. In an exemplary embodiment, the blocking agent is bovine serum albumin.

In some embodiments, the solution comprises one or more of maltodextrin, trehalose, PEG, a blocking agent (e.g. bovine serum albumin), and/or sodium chloride. In exemplary embodiments, one or more of the solution components, e.g., maltodextrin, may be provided as a lyophilized bead or pellet that is suspended upon the addition of a liquid, e.g., water, saline solution, or a liquid sample. For instance, one or more of the solution components may be provided in a spectrophotometric cuvette or a reaction chamber of an analytical rotor as a bead that is suspended into the solution following the addition of a liquid.

In additional embodiments, the LSPR signal may be substantially increased by mixing the first and second detection conjugates with the analyte in the presence of a polymeric accelerant material selected from polyethylene glycol, polyvinylpyrrolidone, polyallylamine, polyethyleneimine, polylysine, polyacrylic acid, polyvinylalcohol, and polyaspartic acid. In an exemplary embodiment, the polymeric material is polyethylene glycol (PEG). In one embodiment, the reaction mixture comprises a polymeric material, e.g., PEG, at a final concentration of about 0.1 mg/mL to about 200 mg/mL. In another embodiment, the reaction mixture comprises a polymeric material, e.g., PEG, at a final concentration of about 0.2 mg/mL to about 100 ng/mL. In yet another embodiment, the reaction mixture comprises a polymeric material, e.g., PEG, at a final concentration of about 0.5 mg/mL to about 10 mg/mL. In yet another embodiment, the reaction mixture comprises a polymeric material, e.g., PEG, at a final concentration of about 2 mg/mL to about 8 mg/mL. In an exemplary embodiment, the reaction mixture comprises a polymeric material, e.g., PEG, at a final concentration of about 2, 3, 4, 5, 6, 7, or 8 mg/mL, inclusive of all values therebetween.

The detection methods of the invention may be used to determine qualitative or quantitative amounts of a target analyte. Such methods are particularly useful for determining the approximate amount of a target analyte in a sample, which can be used inter alia to diagnose certain medical conditions or evaluate the efficacy of a drug therapy. In one embodiment, the quantity of a target analyte can be determined by establishing a standard curve for the particular analyte by measuring changes in optical signals from the metallic nanoparticles as described herein for samples with a known quantity of target analyte; determining the optical signal change for a test sample; and comparing the optical signal change for the test sample to the values obtained for the standard curve. In some embodiments, determining the quantity of a complex between a first reagent and a second reagent comprises comparing the absorbance ratio and/or reaction rate from a test sample to the absorbance ratio and/or reaction rate from one sample with a known quantity of complex, thereby determining the quantity of the complex in the test sample. The quantitative values obtained from test samples may be compared to pre-determined threshold values, wherein said pre-determined threshold values are indicative of either an abnormal or normal level of the target analyte.

The detection methods of the present invention provide a highly sensitive technique for detecting minute quantities of a target analyte in a sample. In some embodiments, amplification of plasmon resonance-based signals can be achieved with gold nanostructure conjugates such that nanogram quantities of target analyte can be detected in a sample. Thus, in one embodiment of the methods, the presence of nanogram quantities of a target analyte is detected. In some embodiments, plasmon resonance-based signals from detection conjugates comprising gold nanoparticles can be amplified using composite metallic nanostructure detection conjugates. Use of gold-coated silver nanostructures conjugated to an analyte-specific antibody may enable the detection of pictogram quantities of the target analyte. Accordingly, in some embodiments of the methods, the presence of picogram quantities of the target analyte is detected. In other embodiments of the methods, the presence of femtogram quantities of the target analyte is detected. Greater sensitivities may be obtained by altering the composition and/or shape of the composite metallic nanostructures.

When incident light is applied to metallic nanostructures, conduction band electrons in the metal oscillate collectively at the same frequency of the incident electromagnetic wave. As a result of these resonance oscillations, the nanostructures strongly absorb and scatter light at a specific wavelength range. For metallic nanostructures comprising noble or transition metals, this wavelength range is in the ultra-violet-visible-infrared spectrum depending on the particular composition of the nanostructures. Thus, light sources for applying electromagnetic energy suitable for use in the methods of the invention can include any source that may apply a wavelength range within the ultraviolet-visible spectrum or ultraviolet-visible-infrared spectrum, including arc lamps and lasers. In some embodiments, the light source may be equipped with a monochromator so that specific wavelengths of light may be applied.

The optical properties of the metallic nanostructures depend on their size, shape, and composition. For instance, solid gold nanoparticles have an absorption peak wavelength ($\lambda_{max}$) from about 515 nm to about 560 nm depending on particle size. Gold spherical nanoparticles having a 30 nm diameter maximally absorb at about 520 nm with $\lambda_{max}$ shifting to longer wavelengths as particle diameter increases. Silver and copper particles have a $\lambda_{max}$ in the ultra-violet/blue or red region (e.g., from about 350 nm to about 500 nm) with increasing particle diameter causing a shift in $\lambda_{max}$ to longer wavelengths. Metallic nanorods have a transverse $\lambda_{max1}$ and a longitudinal $\lambda_{max2}$. Alloys of different metals typically exhibit absorption peaks in an intermediate range between the absorption peaks of the comprising metals. For example, nanostructures comprising a 50/50 alloy of gold and silver exhibit a $\lambda_{max}$ of about 480 nm with increasing amounts of gold causing a shift in the absorption peak to longer wavelengths. The sensitivity of the LSPR signals to changes in the local medium refractive index can be modified by changing the shape or geometry of the nanostructures. For instance, nonspherical particles (e.g. nanoprisms, nanorods, nanoshells, etc.) have increased LSPR sensitivities as compared to spheres. In some embodiments, the optical properties (e.g. absorption/scattering at particular wavelengths) are tailored to a particular application by varying the size, shape, or composition of the metallic nanostructures employed in the detection conjugates.

The interaction between the incident light and the metallic nanostructures can be monitored as reflected light or transmitted light. The amount of the incident light that is absorbed or scattered can be measured as an absorption spectrum in a reflection mode or the absorption spectrum in a transmission mode. In some embodiments, the optical signal measured from the metallic nanostructures can be an optical reflection, an absorbance spectrum, a scattering spectrum, and/or an emission spectrum.

The plasmon coupling between the metallic nanostructures in the detection conjugates resulting from complex formation between the binding partners and target analyte produces a change in the localized surface plasmon resonance spectrum of the metallic nanostructures. For instance, such changes can include an increased optical extinction, an increased optical reflection, and/or increased scattering and/or emission signal. In some embodiments, the change in optical signal indicative of the presence of the target analyte in the sample includes a shift, increase or decrease in optical scattering or a combination of these features. In certain embodiments, the change in optical signal indicative of the presence of the target analyte in the sample is a spectral peak wavelength shift. In certain other embodiments, the change in optical signal indicative of the presence of the target analyte in the sample is the wavelength shift at a position other than the peak. For instance, the change in optical signal indicative of the presence of the target analyte in the sample may be the midpoint spectral wavelength shift, the spectral wavelength shift at the wavelength's base, or the total spectral wavelength shift such as difference spectrum. In one embodiment, the wavelength shift in the optical spectral peak may be a red shift (e.g., a shift to a longer wavelength) within a 200 nm to 1200 nm spectral window. In another embodiment, the wavelength shift in the optical spectral peak may be a blue shift (e.g., a shift to a shorter wavelength) within a 200 nm to 1200 nm spectral window. The changes in optical signals can be measured at a particular time point following a set reaction period. Additionally or alternatively, changes in the optical signal over the reaction period (e.g. rate determinations) may be measured. Both types of measurements can be used for either qualitative or quantitative analysis of a target analyte.

Various means for measuring optical signals at different wavelengths and acquiring extinction, scattering, or emission spectra are known in the art. Any spectrophotometric or photometric instruments are suitable for use in the disclosed methods. Some non-limiting examples include plate readers, Cobas Fara analyzers, and Piccolo xpress® and Vetscan analyzers (Abaxis, Inc., Union City, Calif.), optic fiber readers (e.g., LightPath™ S4 (LamdaGen, Menlo Park, Calif.)), SPR instruments (e.g., Biacore instruments available from GE Healthcare), centrifugal analyzers from Olympus, Hitachi etc.

The present invention also includes an assay complex comprising (i) a first detection conjugate that comprises a metallic nanostructure coupled to a binding partner, (ii) a target analyte, and (iii) a second detection conjugate that comprises a metallic nanostructure coupled to a binding partner, wherein the binding partner in the first detection conjugate is bound to a first epitope on the target analyte and the binding partner in the second detection conjugate is bound to a second epitope on the target analyte, thereby forming a complex comprising the first detection conjugate, target analyte, and the second detection conjugate. In some embodiments, the assay complex is contained within a cuvette adapted for use with a centrifugal rotor. In other embodiments, the assay complex is contained within a reaction chamber in a centrifugal rotor or disc.

Any type of target analyte can be detected using the methods, devices, and assay complexes of the present invention, particularly those that are significant in the diagnoses of diseases. A target analyte can include, but is not limited to, a protein, enzyme, antigen, antibody, peptide, nucleic acid (RNA, DNA, mRNA, miRNA), hormone, glycoprotein, polysaccharide, toxin, virus, virus particle, drug molecule, hapten, or chemical. In some embodiments, the target analyte is a marker or antigen associated with an infectious disease in humans and/or animals. In other embodiments, the target analyte is a marker or antigen associated with a particular physiological state or pathological condition.

In certain embodiments, the target analyte is a pathogenic antigen or antibody to a pathogenic antigen. For instance, the pathogenic antigen can be a viral antigen (e.g., feline leukemia virus, canine parvovirus, foot and mouth virus, influenza virus, hepatitis a, b, c virus, HIV virus, human papilloma virus, Epstein Barr virus, rabies virus, etc.), a bacterial antigen (e.g., *Ehrlichia, Borrelia, Anaplasma, Salmonella, Bacillus, Rickettsia*, etc.), a fungal antigen, or parasitic antigen (e.g., canine heartworm, *Giardia lamblia, Plasmodium falciparum, African trypanosomiasis, Trypanosoma brucei*, etc.). In specific embodiments, the bacterial antigen may be from *Ehrlichia canis, Ehrlichia chafeensis, Ehrlichia ewingii, Borrelia burgdorferi, Anaplasma platys, Anaplasma phagocytophilum, Salmonella enterica, Bacillus anthracis,* and *Rickettsia rickettsii*. In other embodiments, the target analyte is a disease-related antigen or antibody to a disease-related antigen. Disease-related antigens include, but are not limited to, cancer-related antigens or markers (e.g., PSA, AFP, CA125, CA15-3, CA19-9, CEA, NY-ESO-1, MUC1, GM3, GD2, ERBB2, etc.), cardiovascular disease-related antigens or markers (e.g., troponin, C-reactive protein, brain natriuretic peptide, CKMB, fatty acid binding protein, etc.), metabolic-related antigens or markers (e.g., thyroid stimulating hormone, thyroxine, leptin, insulin), or autoimmune disease-related antigens or markers (e.g., auto-antibodies). In certain embodiments, the target analyte is an inflammatory antigen or marker (e.g., C-reactive protein, MRP14, MRP8, 25F9, etc.). In other embodiments, the target analyte is a pregnancy-related antigen or marker (e.g., a fetal antigen, human chorionic gonadotropin).

The present invention also provides a method for preparing composite metallic nanostructures. In one embodiment, the method comprises preparing a first solution comprising a mixture of a polymer and chloroauric acid, preparing a second solution comprising silver or copper nanostructures, and incubating the first solution with the second solution for a period of time, wherein the resulting mixture comprises gold-coated silver nanostructures or gold-coated copper nanostructures. The resulting mixture preferably has a peak absorbance of about 515 nm to about 670 nm, or about 520 nm to about 560 nm. In one embodiment, the resulting mixture has a peak absorbance of about 530 nm to about 545 nm. In another embodiment, the method comprises preparing a first solution comprising a mixture of a detergent such as CHAPS and chloroauric acid, and a solution comprising silver or copper salts, and incubating the first solution with the second solution containing a reducing agent, such as ascorbic acid leading to the formation of composite nanostructures. The size and shape of the nanostructures can be varied by changing the ratio of metals used, concentration of detergent and finally the amount of ascorbic acid used.

The polymer used in the preparation of the first solution can be any one of polyvinylpyrrolidone, polyvinyl alcohol, polyacrylate, polyethylene glycol, polyethyleneimine, polyaspartic acid, polyglutamic acid, various gums, gelatin or mixed polymers comprising any of the foregoing. In one particular embodiment, the polymer is polyvinylpyrrolidone. Different types of coated nanostructures can be obtained by varying the molecular weight of the polymer. Suitable molecular weight ranges of the polymer include from about 5,000 Daltons to about 150,000 Daltons, about 10,000 Daltons to about 100,000 Daltons, from about 20,000 Daltons to about 80,000 Daltons. In some embodiments, the polymer has a molecular weight less than 50,000 Daltons. In other embodiments, the polymer has a molecular weight less than 20,000 Daltons. In certain embodiments, the polymer has a molecular weight of about 10,000 Daltons.

The characteristics of the gold coating can be controlled by adjusting the concentration ratio of polymer to chloroauric acid. For instance, the concentration ratio of polymer to chloroauric acid is from about 100:1 to about 1:100, from about 2:1 to about 5:1, or from about 1.5:1 to about 8:1. In some embodiments, the concentration ratio of polymer to chloroauric acid is 1:1. Suitable concentrations of polymer include, but are not limited to, about 0.1% to about 20% wt/wet in water or ethanol. Suitable concentrations of chloroauric acid include, but are not limited to, about 0.001 M to about 1.0 M, about 0.010 M to about 0.500 M, and about 0.050 M to about 0.100 M.

The coating efficiency and thickness can also be affected by the pH and halide content of the coating solution (i.e. first solution). In certain embodiments, the pH of the solution is kept in a range from about 3 to about 14. The halide content of the solution is, in some embodiments, less than 150 mM. In other embodiments, the halide content of the solution is in the range of about 0 to about 50 mM.

Methods of preparing solutions of silver and copper nanostructures are known to those of skill in the art. For instance, the second solution comprising silver or copper nanostructures can be prepared by any of the methods described in U.S. Patent Publication No. 2012/0101007, U.S. Patent Publication No. 2014/0105982, or U.S. Patent Publication No. 2013/0230717, each of which is hereby incorporated by reference in its entirety. In one embodiment, the second solution comprising silver or copper nanostructures is prepared by mixing a silver or copper source with a reducing agent. A suitable silver source includes a silver salt, such as silver nitrate. Suitable copper sources include copper (II) sulfate, copper (II) chloride, copper (II) hydroxide and copper (II) nitrate, copper (II) acetate and copper (II) trifluoroacetate. Reducing agents that can be reacted with the silver or copper sources to form the nanostructures can include glucose, ascorbic acid, sodium borohydride, and alkaline solutions (e.g. pH greater than 7.5) of polymers such as PVP. In certain embodiments, the reducing agent is ascorbic acid. The desired shape and optical spectral peak of the silver nanostructures or copper nanostructures can be attained by adjusting the ratios or concentrations of reactants as known to those of ordinary skill in the art. By way of example only, high concentrations of the reducing agent can result in pentagonal- and bipyramidal-shaped nanostructures, whereas low concentrations of the reducing agent can result in elongated nanowires or tubes. Depending on the particular shapes of the nanostructures, the second solution comprising silver or copper nanostructures may have a peak absorbance from about 540 nm to about 1000 nm, from about 600 nm to about 700 nm, from about 630 nm to about 680 nm, from about 750 nm to about 850 nm, from about 900 nm to about 940 nm, from about 580 nm to about 620 nm, or from about 550 nm to about 750 nm. In certain embodiments, the second solution comprising silver nanostructures has a peak absorbance of about 600 nm (i.e. 595 nm to 605 nm, inclusive). In some embodiments, the second solution comprising copper nanostructures has a peak absorbance of about 585 nm (i.e. 580 nm to 590 nm, inclusive). In some embodiments the peak absorbance of a solution comprising copper nanostructures is greater (i.e. red-shifted) than the peak absorbance of a solution comprising silver nanostructures of a similar size and shape.

In some embodiments, the incubation period of the first solution with second solution is at least 12 hours. In other embodiments, the incubation period of the first solution with second solution is greater than 24 hours, preferably greater than 48 hours, more preferably at least 72 hours. Changes in the peak absorbance of the reaction mixture can be monitored during the incubation period to adjust the incubation time accordingly. For example, shifts of the peak absorbance to shorter wavelengths, for instance in the 520 nm to 550 nm region, can indicate that the gold-coated nanostructures have stabilized. In certain embodiments, stability of the resulting nanostructures to sodium chloride (e.g., 0.25-1M) is used to indicate a proper coating of the nanostructures. CTAB-coated particles such as nanorods are resistant to sodium chloride.

In certain embodiments, the present invention provides methods of synthesizing nanostructures having optical densities greater than about 50/mL. In one embodiment, the methods comprise mixing a polymer as described herein with chloroauric acid, stirring the mixture at a set temperature for a first period of time, adding ascorbic acid to the mixture, and incubating the mixture for a second period of time. The size and shape of the nanostructures is dictated by the concentration ratio of polymer to chloroauric acid and the temperature and time of incubation. The concentrations of polymer and chloroauric acid can be in the ranges described above. The temperature can be adjusted based on the size and shape of the nanostructures desired, but may be in the range of about 4° C. to about 100° C. Similarly, the incubation period (i.e. first period of time) can be adjusted based on the desired properties of the nanostructures, but may range from about 15 minutes to one day.

In some embodiments, about 0.1 to 1 part of ascorbic acid (e.g. about 1 to 5 M) is added to the mixture following the first incubation period. The second incubation period following addition of the ascorbic acid may be from about 1 to about 24 hours. Without being bound by theory, addition of ascorbic acid provides a substantial increase in the quantity of nanostructures produced.

In certain embodiments, the methods further comprise adding or doping the mixture with about 1 to about 100 parts of gold chloride (e.g. about 0.001 M to 1M) or silver nitrate (e.g. about 0.001 M to 1M) or other metal (e.g. noble metal, transition metal, alkali metal, or lanthanide). This doping step can further increase the resonance intensity of the resulting nanostructures. In some embodiments, the gold chloride, silver nitrate, or other metal is added to the mixture before ascorbic acid is added to the reaction. In other embodiments, the gold chloride, silver nitrate, or other metal is added to the mixture following the addition of ascorbic acid. The order of addition of the metal and ascorbic acid may be adjusted to tailor the resulting nanostructures to a desired shape and size.

In some embodiments, the present disclosure provides methods for synthesizing composite nanoparticles. In certain embodiments, silver/gold nanoparticles are synthesized in a single vessel by adding predetermined quantities of the following reagents in succession and with thorough mixing: (1) a surfactant (e.g., ionic [anionic, cationic or zwitterionic], or non-ionic) or capping agent such as 3-((3-Cholamidopropyl) dimethylammino)-1-propanesulfonate (CHAPS), SDS, Tween, Triton, or any of the sulfobetaine detergents, (2) gold chloride, (3) water, (4) silver nitrate, (5) trisodium citrate and finally (6) ascorbic acid is added to initiate the formation of nanoparticles. In other embodiments, the nanoparticles are synthesized in a single vessel by adding predetermined quantities of the following, in the following order: (1) a surfactant or capping agent such CHAPS, SDS, Tween, Triton, CTAB, or any of the sulfobetaine detergents, (2) gold chloride, (3) silver nitrate, (4) trisodium citrate, (5) water, and (6) a reductant. In some embodiments, the reductant is made up of CHAPS, ascorbic acid, trisodium citrate, and water. In further embodiments, the reductant is made up of about 200 mg CHAPS, about 4 g ascorbic acid, about 117.6 mg trisodum citrate, and about 15.68 g water. In some embodiments, about 1 mL of aqueous 1% (wt/wt) CHAPS is mixed sequentially with about 0.25 mL of 0.1M gold chloride, about 0.5 mL of 0.02M silver nitrate, about 0.05 mL of 1M trisodium citrate, about 6.2 mL of water, and about 2 mL of the reductant. Changing the concentrations of various active ingredients such as metallic salts, capping agents, reductants and pH of the solution results in different particle types (e.g., nanospheres, nanostars or nanorods) and different composition of the nanoparticles.

In some embodiments, nanostars are formed by mixing, in order, water, cetyltrimethylammonium bromide (CTAB), gold chloride, ascorbic acid, and pre-formed gold nanosphere seeds. In further embodiments, about 0.825 mL of water, about 0.1 mL of 20% CTAB, about 0.025 mL of 0.1 M gold chloride, about 0.05 mL of 1M ascorbic acid, and about 0.05 mL of gold nanosphere seeds are mixed in that order. The age of the seeds and the ratio of seeds to the metallic ions influence the geometry and thus the optical spectra of nanoparticles.

The formation of nanomaterials using the methods provided herein is essentially complete within minutes but may be allowed to reach equilibrium overnight. The synthesis of nanoparticles can be monitored by spectroscopy and confirmed by scanning or transmission electron microscopy.

In some embodiments, the size and thus the optical properties can be changed by altering the concentration of the surfactant or capping agent, ascorbic acid, trisodium citrate, gold chloride and/or silver nitrate. The size of nanostars synthesized increases with increasing silver content up to a certain point and then it decreases. These changes are reflected in the LSPR peak of the synthesized nanostars as the peak red-shifts at increasing silver/gold ratio but then starts to blue shift at molar ratios of Gold:Silver::5:2. The final concentrations of the chosen detergent in the reaction mixture can be varied from 0.05-5% with the smaller particles predominating at higher concentrations of the detergent. Increasing the concentrations of ascorbic acid produces smaller nanostars with the final concentration of ascorbic acid varying from 0.05 to 0.2M. Similarly, increasing concentration of trisodium citrate from 10 mM to 100 mM decreases the nanostar sizes.

In some embodiments, gold-silver nanoalloys may be synthesized under alkaline reduction conditions by mixing CTAB (e.g., CTAB dissolved in alcohol) with gold chloride and silver nitrate. In some embodiments, nanoalloy formation may be induced by mixing, in order, water, CTAB, gold chloride (0.5 mM to 5 mM), silver nitrate (20% to 80% of gold), ascorbic acid (10 mM to 200 mM) or a reductant containing ascorbic acid, trisodium citrate and CHAPS, and NaOH (50% to 200% of ascorbic acid). In further embodiments, nanoalloys are formed by mixing about 0.825 ml of water, about 0.1 ml of 20% CTAB prepared in isopropanol, about 0.025 ml of 0.1M gold chloride, about 0.005-0.025 ml of 0.1M silver nitrate, about 0.05 ml of 1M ascorbic acid, and about 0.05 ml of 1M NaOH. The concentrations of CTAB can be varied from 0.05M to 0.2M with lower concentrations favoring higher content of nanostars synthesized. Acidic pH favors formation of nanorods and higher aspect ratios are obtained at decreasing pH.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

All patent and non-patent documents referenced throughout this disclosure are incorporated by reference herein in their entirety for all purposes.

EXAMPLES

Example 1. Direct Assay Utilizing Amplification of LSPR Signals

In this example, a blank reaction is setup by adding a solution containing colloidal conjugate of anti-heartworm polyclonal antibody, a suitable dispersing medium such as phosphate buffered saline, and a sample devoid of heartworm antigen. The spectral changes are recorded over a period of time. A set of positive controls is then setup by adding known quantities of heartworm antigen to the reaction solutions used in the blank solution above. Alternatively, a blank reaction is recorded and then known quantities of heartworm antigen are added to prepare a calibration curve correlating shift in spectral scan with concentrations of antigen. This calibration curve is then used to calculate the quantity of heartworm antigen in an unknown sample. The shift in spectral scan means (i) a change in $\lambda_{max}$, (2) difference spectrum between positive and negative samples, or (3) derivative spectra.

Example 2. Sandwich Assay Utilizing Amplification of LSPR Signals

Sandwich assays are most suitable where an analyte displays at least two distinct binding sites (epitopes of an antigen) with each site binding to a specific binding partner. Thus, in this example, an antibody directed towards one epitope of CRP is immobilized on the gold and/or silver nanoparticles and the second antibody directed towards a non-overlapping epitope is labeled with colloidal gold and/or silver. This setup allows measurement of the CRP antigen as the amount of CRP antigen in the sample determines the extent of spectral change. The spectral change is also seen when the second antibody is not labeled but the change is several orders of magnitude lower. The metallic composition of the nanoparticles may be changed to optimize the reaction conditions.

Example 3. Performing Assays in a Rotor

Direct competitive assays or sandwich assays may be performed in a centrifugal rotor, such as a rotor described in U.S. Pat. Nos. 5,061,381, 5,122,284, 5,186,844, 5,304,348, 5,457,053, and 5,693,233. In this case, the nanoparticle conjugates of the two pairing monoclonal antibodies or a polyclonal antibody mixture that binds to more than one epitope are added as lyophilized beads. The solution phase LSPR assay works both with monoclonal and polyclonal antibodies.

Example 4. Enhancement of LSPR Signals by Polyethylene Glycol or Similar Polymers The data presented in FIGS. 4 and 9A-9C show that the LSPR signals are substantially increased in the presence of polyethylene glycol. PEG with different molecular weights may be used at optimized concentrations to obtain desired selectivity in a given assay. One may substitute PEG with polyvinylpyrrolidone or similar polymeric materials to obtain optimized reaction conditions for a given set of nanoparticles and/or the set of specific binding partners.

Example 5. Addition of Maltodextrin Improves Assay Sensitivity

Figure 16:
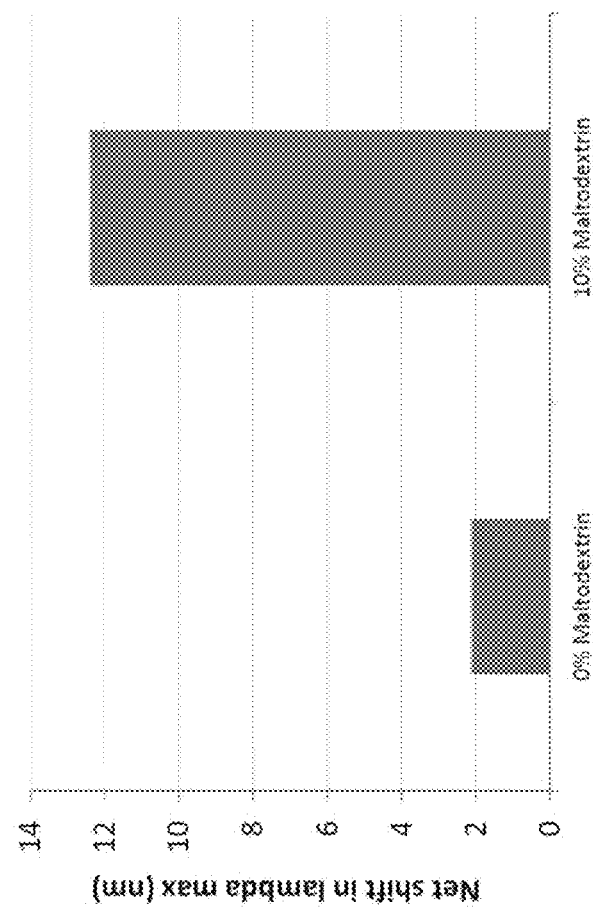
FIG. 16. Illustrates high positive effect of maltodextrin on LSPR signal.
Figure 17:
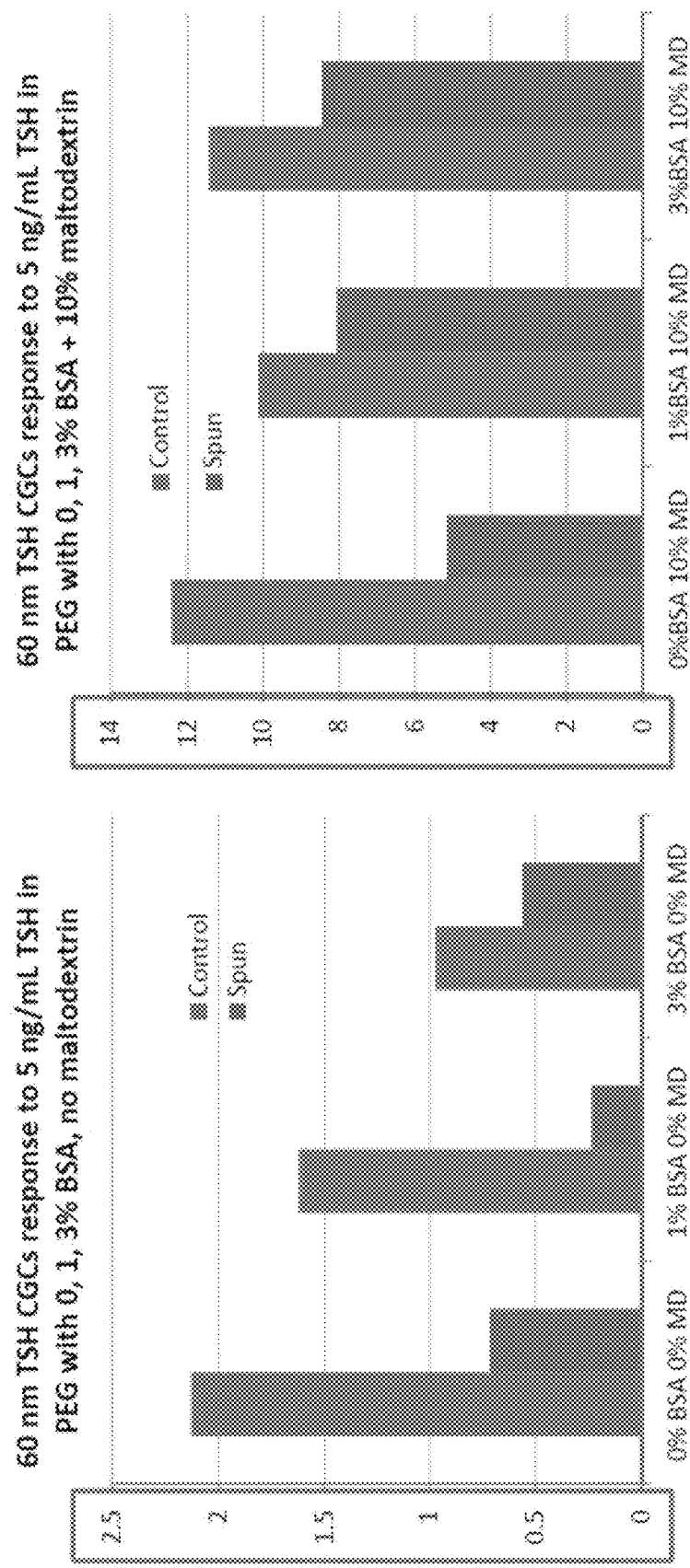
FIG. 17. Illustrates how maltodextrin and BSA decrease sedimentation in the analytical rotor and maintain high LSPR signal.
Figure 18:
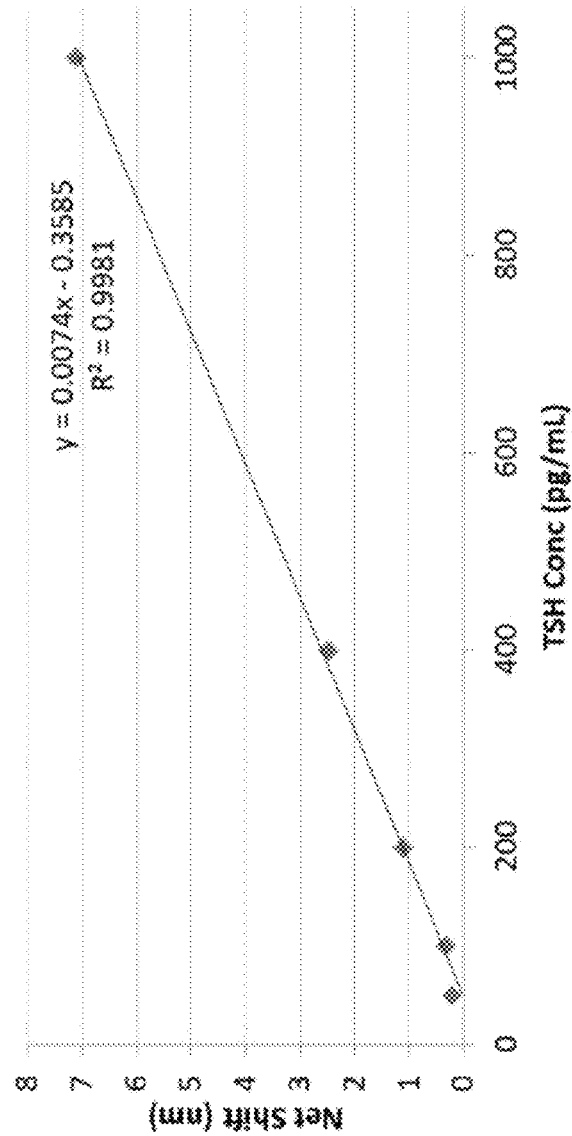
FIG. 18. Illustrates pg/ml detection of TSH under various concentrations of BSA, PEG and maltodextrin.

A number of experiments were carried out to determine the effects of various sugars and other agents to minimize the sedimentation effects and retain the LSPR signals. As shown in FIG. 16, maltodextrin surprisingly boosted the signal which was further improved by the presence of BSA. By contrast, the strength of the LSPR signal was not as strong when trehalose, sorbitol, or cyclodextrin was added (data not shown). In addition, the sedimentation problem was also solved via the addition of maltodextrin and BSA (FIG. 17). Approximately 50 pg/ml of TSH was detectable with particular quantities of PEG, BSA and maltodextrin (FIG. 18).

Example 6. Synthesis of Gold Nanostars and Gold-Silver Alloy Particles and Uses Thereof Novel methods were utilized to synthesize nanomaterials for use in plasmonic assays such as solution-phase plasmonic assays described herein.

CHAPS-coated nanostars or CTAB-coated nanostars were prepared using the following methods. For CHAPS-coated nanostars, 1 ml of aqueous 1% (weight/weight) CHAPS (3-((3-cholamidopropyl) dimethylammonio)-1-propanesulfonate) was prepared in a suitable vessel. 0.25 ml of 0.1M gold chloride, 0.5 ml of 0.02M silver nitrate, 0.05 ml of 1 M trisodium citrate, 6.2 ml of water and finally 2 ml of Reductant (200 mg CHAPS, 4 g ascorbic acid, 117.6 mg trisodium citrate, 15.68 g water) were stirred into the vessel sequentially and mixed well for at least one hour. After dilution to 1:20 in water, the optical spectrum was read. In some embodiments, the size and thus the optical properties can be changed by altering the concentration of CHAPS, ascorbic acid, trisodium citrate, gold chloride and silver nitrate.

For CTAB-coated nanostars, Cetyltrimethylammonium bromide (CTAB) was dissolved in isopropanol at a concentration of 20% (wt/wt). All other reagents were aqueous. Nanostar formation was induced by mixing in order: 0.825 ml of water, 0.1 ml of 20% CTAB, 0.025 ml of 0.1M gold chloride, 0.05 ml of 1M ascorbic acid and finally 0.05 ml of preformed gold nanosphere seeds. In some embodiments, the size and thus the optical properties can be changed by altering the concentration of components. Aqueous solutions of CTAB at 30° C. produced nanorods when fresh seeds were used for seeding nanorods. CTAB solutions prepared in isopropanol can be used at room temperature but favor the synthesis of nanostars over nanorods.

Gold-silver nanoalloys were synthesized under alkaline reduction conditions by mixing CTAB dissolved in isopropanol with gold chloride and silver nitrate. Nanoalloy formation was induced by mixing in order: water (to make a total of one ml reaction volume), 0.2 ml of 20% CTAB (in isopropanol), 0.025 ml of 0.1M gold chloride, 0-0.05 ml of 0.02M silver nitrate, 0.02 ml of reductant containing ascorbic acid, CHAPS and trisodium citrate, and finally 0.05 ml of 1M NaOH. In some embodiments, reductants contain CHAPS, trisodium citrate, and ascorbic acid. Acidic pH favors production of nanostars and nanorods, depending on the age of the seeds.

Figure 10:
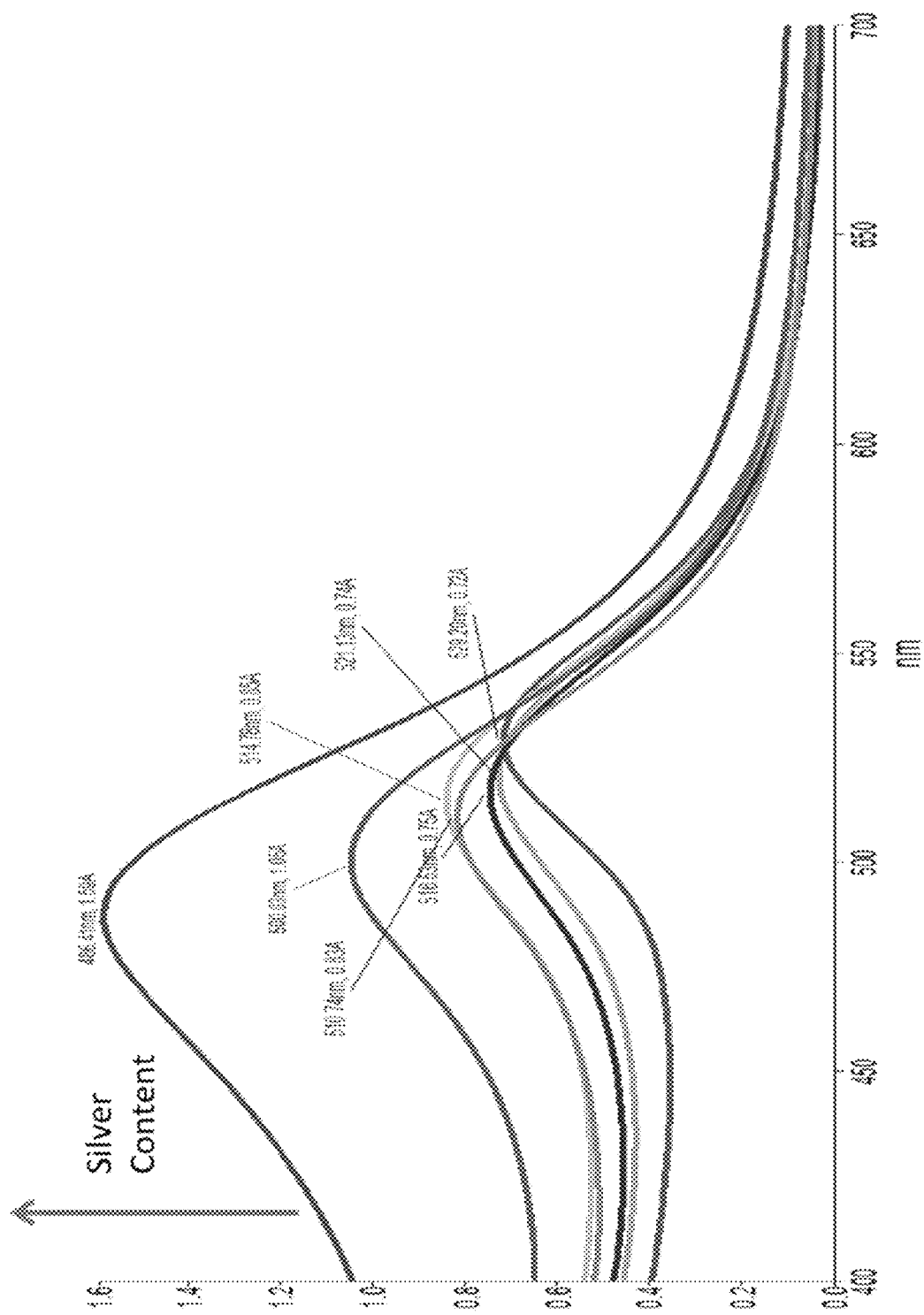
FIG. 10. Illustrates the optical spectra of gold/silver alloy nanoparticles synthesized as follows: Gold chloride was reacted with CTAB before the addition of silver nitrate followed by the addition of ascorbic acid and finally sodium hydroxide.
Figure 11:
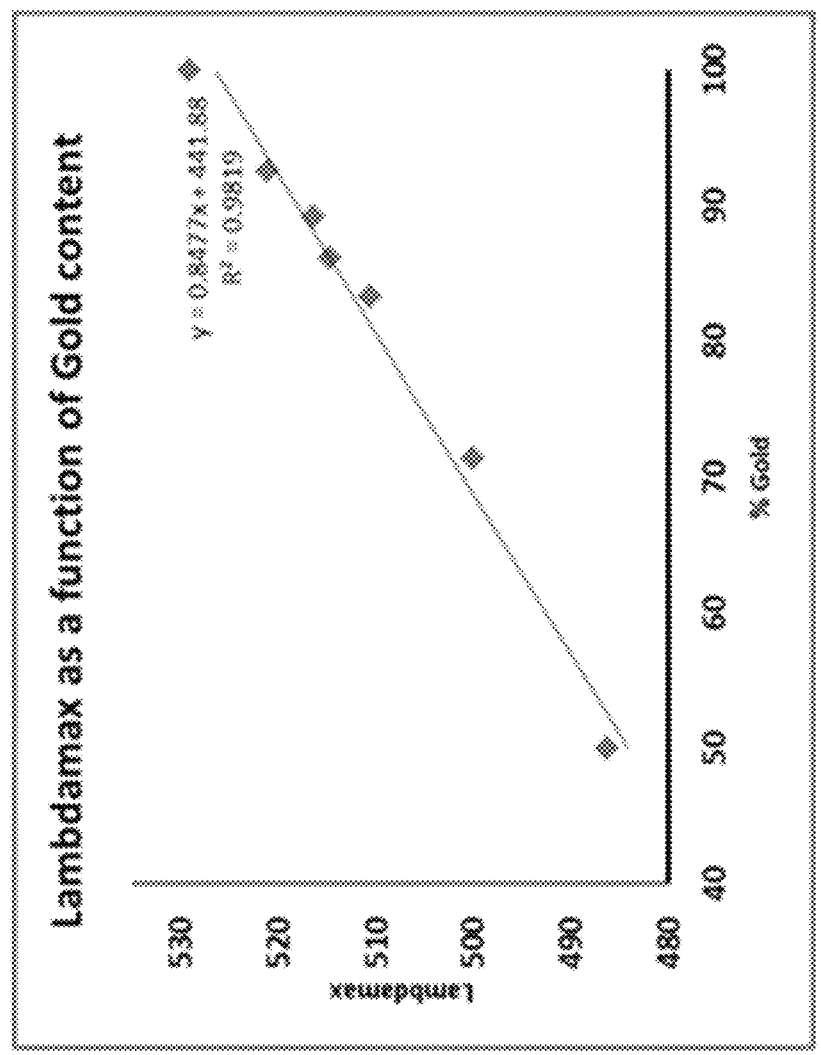
FIG. 11. Illustrates linear blue shift in $\lambda_{max}$ with increasing silver content in the nanoalloy particles.

The optical spectra of gold/silver alloy nanoparticles synthesized by reacting gold chloride with CTAB before the addition of silver nitrate followed by the addition of ascorbic acid and finally sodium hydroxide is provided in FIG. 10. Increasing the silver content in the nanoalloy particles results in a linear blue shift in $\lambda_{max}$ and increasing the gold content in the nanoalloy particles results in a red shift, as shown in FIG. 11.

Figure 13:
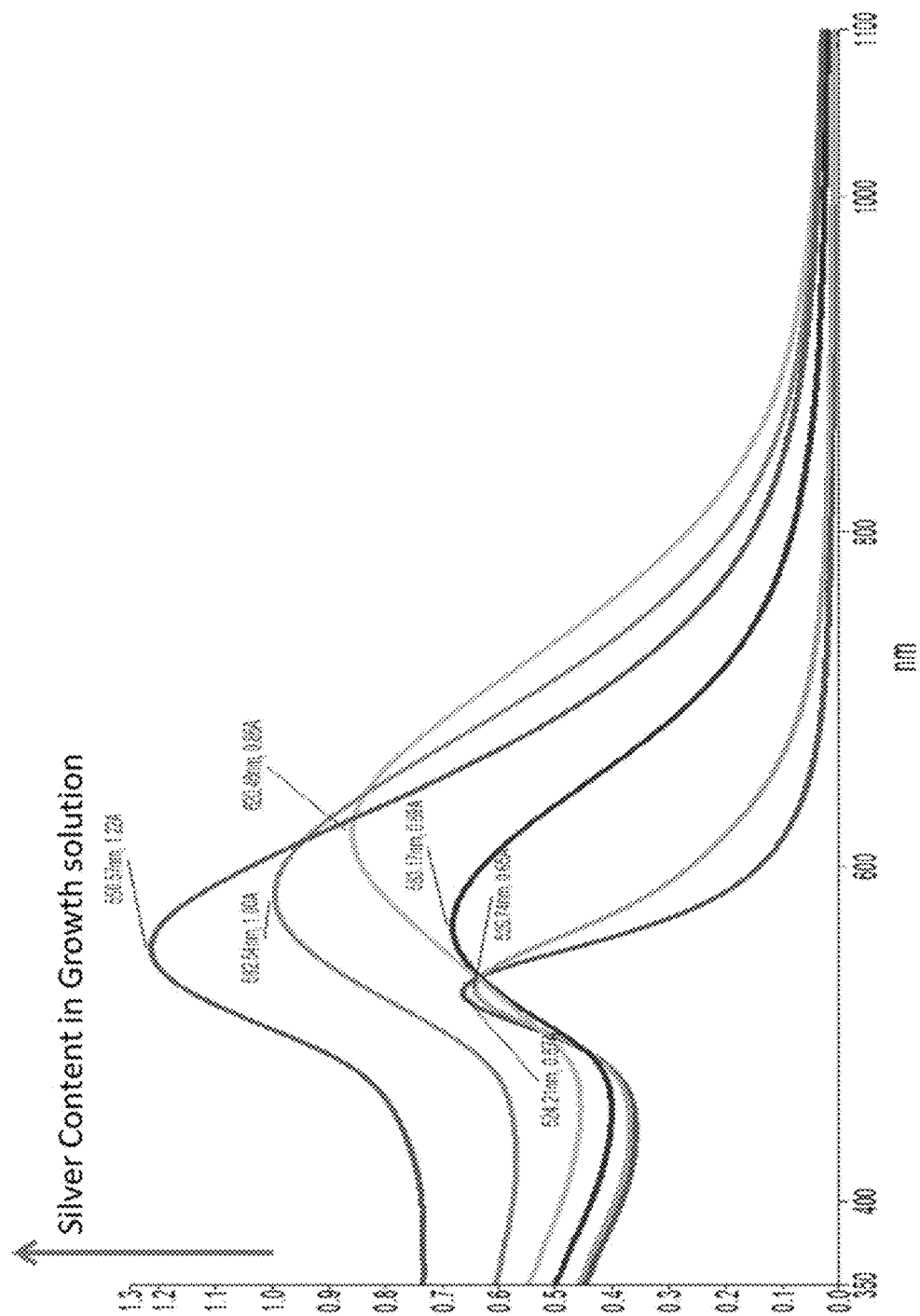
FIG. 13. Illustrates the optical spectra of gold/silver nanostars capped with CHAPS. Gold chloride is added to CHAPS prior to the addition of silver nitrate and trisodium citrate. The nanostar formation is induced by the addition of a reducing solution containing ascorbic acid, CHAPS and trisodium citrate $\lambda_{max}$ red-shifts up to a certain concentration of silver and then blue-shifts thereafter. Different sized nanostars are thus produced by changing the ratio of gold to silver in the reaction medium.

To prepare gold/silver nanostars capped with CHAPS, gold chloride was added to CHAPS prior to the addition of silver nitrate and trisodium citrate. The nanostar formation was induced by the addition of a reducing solution containing ascorbic acid, CHAPS and trisodium citrate. The optical spectra of the gold/silver nanostars capped with CHAPS are shown in FIG. 13. $\lambda_{max}$ red-shifted up to a certain concentration of silver and then blue-shifted thereafter. Thus, different sized nanostars were produced by changing the ratio of gold to silver in the reaction medium.

Antibodies were attached to nanostars or nanoalloys using the following method. A suitable volume of nanostar or nanoalloy solution was centrifuged at a suitable g force. Supernatant was removed carefully and replaced with equal volume of 1% CHAPS. A 1:20 dilution in water was read for spectrum and OD at $\lambda_{max}$. In a 2 ml microfuge tube, water, 0.5M borate (pH 9.2), 1% CHAPS, washed nanostars/nanoalloy from the step 1, and desired antibody was added, in that sequence. The quantities of solutions were adjusted so that the final concentration of CHAPS was 0.1%, borate was 0.05 to 0.1M, particle OD was 2 per ml, and the antibody concentration was 1-10 µg/OD. After 5-10 min incubation, equal volume of conjugate diluent CG (3×PBS, 1% BSA, 2% CHAPS, and 0.1% sodium azide) was added and mixed well, then centrifuged at 5000 g for 10 min. supernatant was removed, and the conjugate was resuspended in the conjugate diluent CG to the original volume. The centrifugation step was repeated one time, and the final pellet was resuspended in ⅕ of the original volume of conjugate diluent CG. The OD spectrum of the 1:10 dilution was read. At this point, the conjugates are ready for therapeutics or use in immunoassays. As known in the literature, the antibodies are attached to the as-synthesized nanoparticles by adding antibodies to the diluted solutions of nanoparticles.

Figure 12:
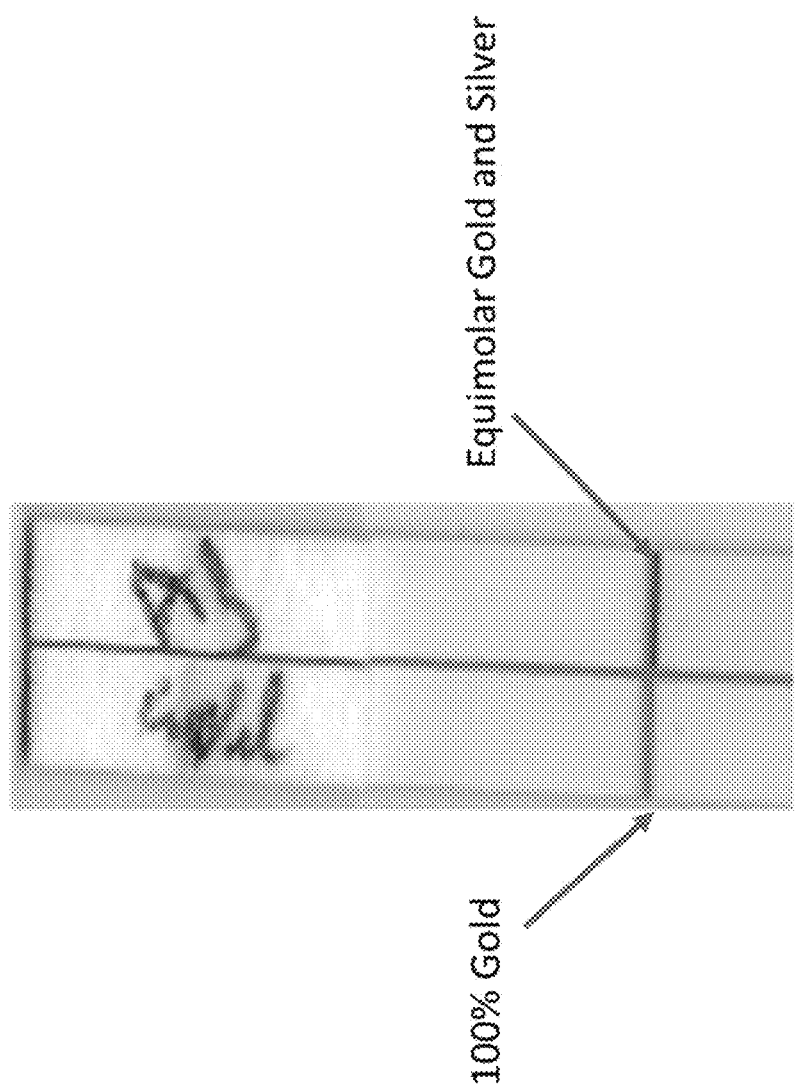
FIG. 12. Illustrates immunoreactivity of mouse IgG conjugates with gold and gold/silver alloy nanoparticles. Conjugates were synthesized by passive adsorption of the mouse IgG on to gold or alloy particles. These were tested for reactivity with Protein A striped on a lateral flow nitrocellulose strip.

FIG. 12 shows the immunoreactivity of mouse IgG conjugates with gold and gold/silver (50%/50% equimolar) alloy nanoparticles. Conjugates synthesized by passive adsorption of the mouse IgG on to gold or alloy particles were tested for reactivity with Protein A striped on a lateral flow nitrocellulose strip.

Figure 14:
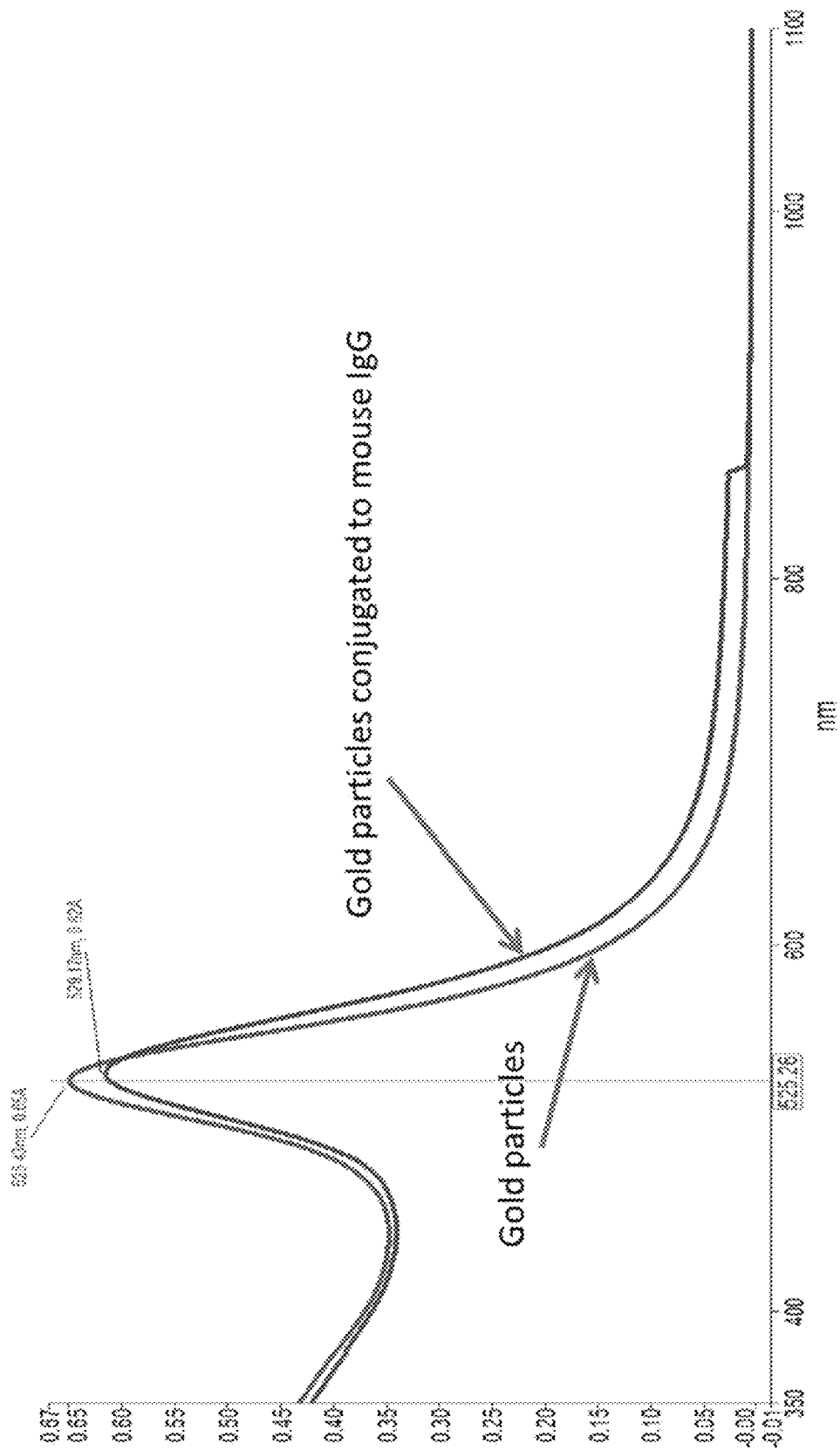
FIG. 14. Illustrates peak-shift to the red upon binding of mouse IgG to gold only nanoparticles produced in the absence of silver.
Figure 15:
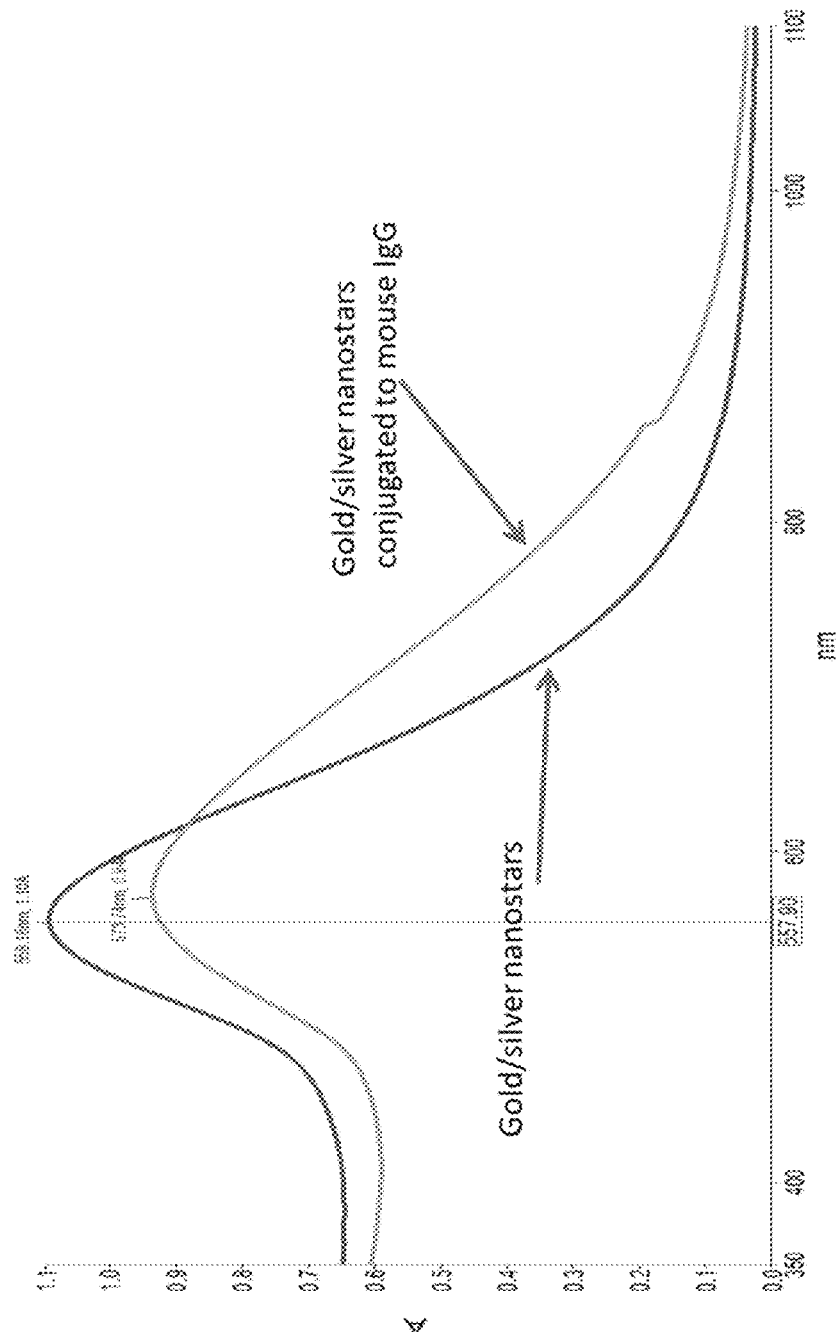
FIG. 15. Illustrates much larger peak-shift to the red upon binding of mouse IgG to gold/silver nanostars produced in the presence of ~37.5% silver.

The gold/silver nanostars exhibited a much larger peak-shift to the red upon binding mouse IgG, relative to gold-only nanoparticles produced in the absence of silver. The peak-shift to the red upon binding of mouse IgG to gold only nanoparticles is shown in FIG. 14, and the larger peak-shift to the red upon binding of mouse IgG to gold/silver nanostars produced in the presence of ~37.5% silver is shown in FIG. 15.

In some embodiments, the centrifugation conditions, ionic strength, pH and antibody to nanomaterial ratio may be optimized for each type of antibody-nanomaterial combination. Alternative methods for conjugation using covalent linkages are well known to those skilled in the art.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of detecting a target analyte in a sample comprising:
    (a) mixing said sample with a first detection conjugate and a second detection conjugate, wherein each of said first and second detection conjugates comprises a metallic nanostructure coupled to a binding partner, wherein said metallic nanostructure comprises a gold nanoparticle coated with a capping agent that includes 3-((3-cholamidopropyl) dimethylammino)-1-propanesulfonate ("CHAPS"), and wherein said binding partner is capable of specifically binding to said target analyte to form a complex between said first detection conjugate, said analyte, and said second detection conjugate;
    (b) exposing the complex to a light source at a wavelength range within the ultraviolet-visible-infrared spectrum; and
    (c) measuring an optical signal from the complex, wherein a change in the optical signal indicates the presence of said target analyte in said sample.

2. The method of claim 1, wherein said metallic nanostructure has a geometry of a nanostar.

3. The method of claim 1, wherein said nanoparticle comprises an alloy of gold and silver.

4. The method of claim 1, wherein the optical signal is reflectance, an absorbance spectrum, a scattering spectrum, or an emission spectrum.

5. The method of claim 1, wherein the change in the optical signal comprises a spectral peak wavelength shift or a total spectral wavelength shift.

6. The method of claim 5, wherein the total spectral wavelength shift is a difference spectrum.

7. The method of claim 1, wherein the presence of nanogram quantities of the target analyte is detected.

8. The method of claim 1, wherein step (a) is performed in a spectrophotometric cuvette, an analytical rotor, a microwell plate, a clinical analyzer, a flow chamber, on the tip of an optical fiber, or in a transparent gel.

9. The method of claim 1, wherein the binding partner is a biological macromolecule.

10. The method of claim 9, wherein the biological macromolecule is selected from an antibody or a fragment thereof, an antigen, a receptor, a ligand, a polynucleotide, an aptamer, a polypeptide, a polysaccharide, a lipopolysaccharide, a glycopeptide, a lipoprotein, or a nucleoprotein.

11. The method of claim 1, wherein each of said first and second detection conjugates comprises an antibody binding partner.

12. The method of claim 11, wherein said antibodies of said first and second detection conjugates bind different epitopes on said target analyte.

13. The method of claim 1, wherein said target analyte is a protein, an enzyme, an antigen, an antibody, a peptide, a nucleic acid, a hormone, a glycoprotein, a polysaccharide, a toxin, a virus, a virus particle, a drug molecule, a hapten, or a small molecule chemical compound.

14. The method of claim 1, wherein said target analyte is a pathogenic antigen or an antibody to a pathogenic antigen.

15. The method of claim 14, wherein the pathogenic antigen is a viral antigen.

16. The method of claim 14, wherein the pathogenic antigen is a bacterial antigen.

17. The method of claim 16, wherein the bacterial antigen is *Ehrlichia canis, Ehrlichia chafeensis, Ehrlichia ewingii, Borrelia burgdorferi, Anaplasma platys, Anaplasma phagocytophilum, Salmonella enterica, Bacillus anthracis*, or *Rickettsia rickettsia*.

18. The method of claim 14, wherein the pathogenic antigen is a fungal antigen or a parasitic antigen.

19. The method of claim 1, wherein step (a) of mixing occurs in the presence of a polymeric material selected from polyethylene glycol, polyvinylpyrrolidone, polyallylamine, polyethyleneimine, polylysine, polyacrylic acid, polyvinylalcohol, and polyaspartic acid.

20. The method of claim 19, wherein the polymeric material is polyethylene glycol.

21. The method of claim 1, wherein step (a) of mixing occurs in the presence of maltodextrin and bovine serum albumin.

22. The method of claim 21, wherein the final concentration of maltodextrin in the mixture of step (a) is about 2% to about 20% wt/vol.

23. The method of claim 21, wherein the final concentration of bovine serum albumin in the mixture of step (a) is about 1% to about 5% wt/vol.

24. An analyte detection device comprising:
a first detection conjugate, wherein the first detection conjugate comprises a metallic nanostructure coupled to a binding partner that is capable of specifically binding to a target analyte if present in a sample; and
a second detection conjugate, wherein the second detection conjugate comprises a metallic nanostructure coupled to a binding partner that is capable of specifically binding to the target analyte if present in the sample,
wherein the metallic nanostructure in each of the first detection conjugate and the second detection conjugate comprises a gold nanoparticle coated with a capping agent that includes 3-((3-cholamidopropyl) dimethylammino)-1-propanesulfonate ("CHAPS").

* * * * *